United States Patent [19]

Haraga et al.

[11] Patent Number: 5,292,479
[45] Date of Patent: Mar. 8, 1994

[54] AIR TREATMENT BY MULTI-STACKED PLATE ASEMBLY

[75] Inventors: Hisato Haraga; Hajime Miyazaki; Yasuo Hamada; Katsushi Akamatsu; Ayako Hirano, all of Kanagawa, Japan

[73] Assignee: Toto Ltd., Fukuoka, Japan

[21] Appl. No.: 914,445

[22] Filed: Jul. 15, 1992

[30] Foreign Application Priority Data

| Nov. 27, 1990 | [JP] | Japan | 2-326420 |
| Feb. 27, 1991 | [JP] | Japan | 3-33010 |
| Feb. 27, 1991 | [JP] | Japan | 3-33066 |

[51] Int. Cl.$^5$ .............. A61L 09/00; E03D 09/052; B01D 45/14; B01D 53/02
[52] U.S. Cl. .............. 422/5; 422/4; 422/120; 422/122; 422/124; 422/125; 4/216; 4/217; 55/317; 55/400; 55/403; 55/408
[58] Field of Search .............. 422/4, 5, 120, 122–125, 422/306; 4/228.1, 216, 217; 55/317, 400, 403, 408

[56] References Cited

U.S. PATENT DOCUMENTS

| 3,260,039 | 7/1966 | Brown et al. | 55/403 |
| 4,382,804 | 5/1983 | Mellor | 55/400 X |
| 4,556,539 | 12/1985 | Spector | 422/5 X |
| 4,999,302 | 3/1991 | Kahler et al. | 422/122 X |
| 5,057,128 | 10/1991 | Panzica et al. | 55/400 X |
| 5,145,648 | 9/1992 | Miyahara et al. | 422/124 |

FOREIGN PATENT DOCUMENTS

| 2176328 | 7/1990 | Japan | |
| 3229614 | 10/1991 | Japan | 422/124 |

Primary Examiner—Robert J. Warden
Assistant Examiner—E. Leigh Dawson
Attorney, Agent, or Firm—Thomas R. Morrison

[57] ABSTRACT

Rotatable circular plates are stacked apart to form thin air layers therebetween. Rotation of the circular plates moves air over an air treatment material: catalyst or adsorbent. In one embodiment, the air treatment material is affixed to the surface of the circular plates. In another embodiment, the circular plates are formed from the air treatment material. The increased velocity of air relative to the circular plates causes separation of laminar flow, promotes boundary-layer turbulence near the plate surfaces, and promotes propagating stall in the air layers. These phenomena enhance the contact between the flowing air and the air treatment material.

23 Claims, 21 Drawing Sheets

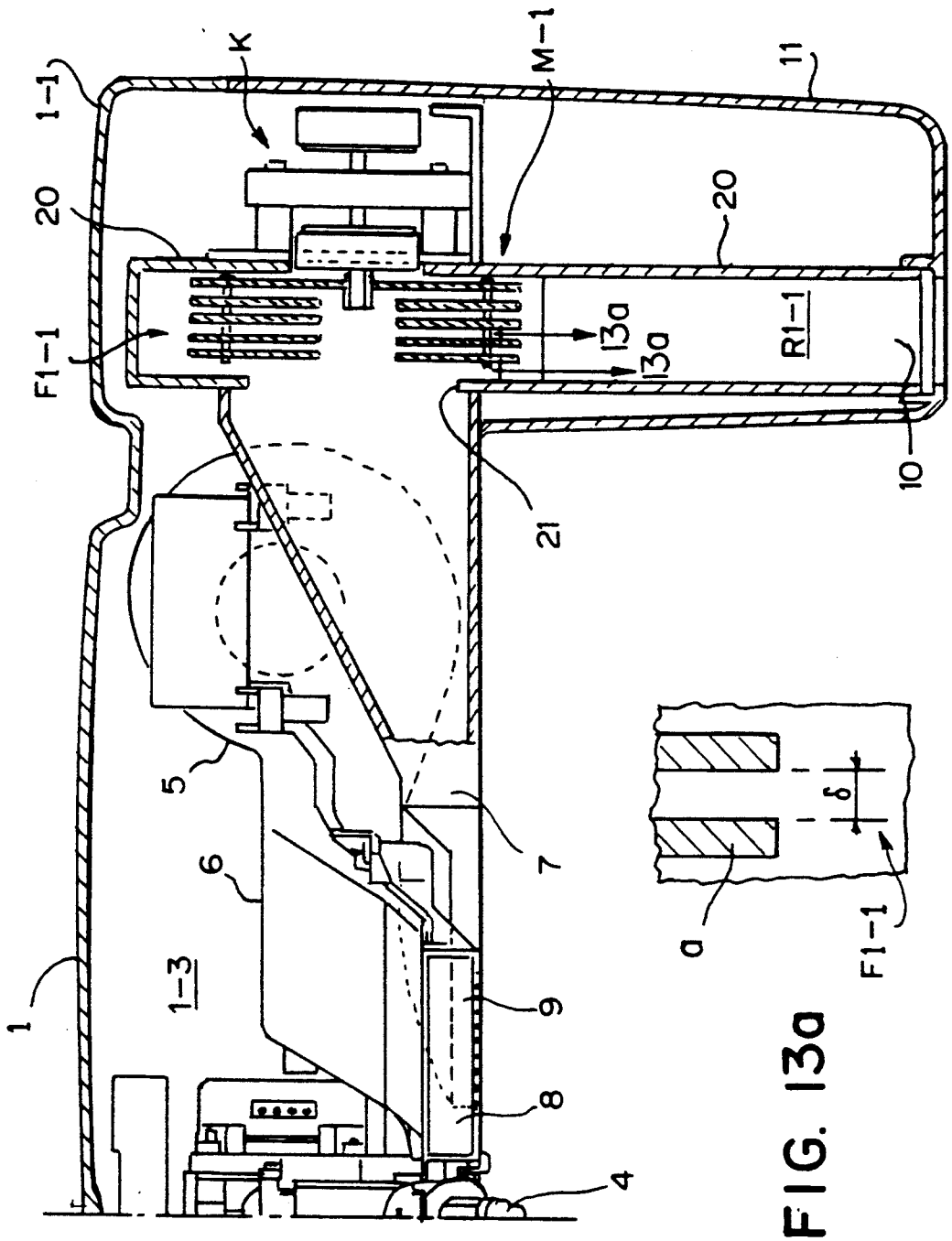

AIR TREATMENT BY MULTI-STACKED PLATE ASEMBLY

TECHNICAL FIELD

This invention relates to a process for air treatment by a multi-layered or multi-stacked rotatable plate assembly.

BACKGROUND ART

Hitherto, there have been practiced a number of air treatments by various means, for example, removal of ozone from ozone-containing air by ozone-decomposing means using an ozone decomposition catalyst, deodorizing of odoriferous air by odor-eliminating means using a deodorant, dehumidification of moist air by hygroscopic means using a drying agent, removal of dust from air containing tobacco smoke or the like by adsorptive removal means using an adsorbent, and addition of fragrance to air by fragrance-releasing means using a fragrant agent.

In some cases, the catalyst, deodorant, drying agent, fragrant agent, adsorbent or the like having the function of treating air as above is formed in a honeycomb shape and disposed in a stream of air to achieve the desired treatment. In other cases, surfaces of a sirocco fan or axial fan used for blowing air are coated with the deodorant or the like having the air-treating function, or, alternatively, the sirocco fan or axial fan itself is formed of a material having a drying function.

The conventional air treatment processes, however, had the following problems.

First, where a deodorant or the like having an air-treating function and formed in a honeycomb shape is placed in a stream of air so as to treat the air, in general, an improvement in the air-treating function per unit volume of the honeycomb-shaped deodorant or the like requires either a marked narrowing of the passage space in the honeycomb (so-called honeycomb pitch) to increase the surface area of the deodorant or the like, or an increase in the length of the passage formed by the honeycomb-shaped deodorant or the like to prolong the dwell time of air in contact with the deodorant or the like. The narrowing of the passage space involves an increase in the passage resistance in the honeycomb-shaped deodorant or the like, leading to the need for a higher fan capacity. An increase in fan capacity requires either a higher rotational frequency, which results in greater noise, or a larger fan size. On the other hand, an increase in the passage length requires the honeycomb-shaped deodorant or the like to be formed in a larger size.

Besides, these air treatment systems have been large and complicated in construction because they are composed of two members, namely, a fan member and the honeycomb-shaped deodorant o the like.

Secondly, where the impeller itself of a sirocco fan or axial fan is formed of a deodorant or the like having an air-treating function, an improvement in the air-treating function per unit volume of the impeller can be accomplished by various methods, for instance, by increasing the number of vanes or the length of vanes so as to prolong the dwell time of air. In this case, the passage resistance between the vanes is increased, with the attendant great reduction in the air flow rate across the fan. It is therefore necessary to contrive a higher fan capacity by an increased rotational frequency, an increased fan size or the like.

As a result, these air treatment systems have been accompanied by the problem of noise due to an increased rotational frequency or the problem of a large fan size.

It is accordingly an object of this invention to provide a process for air treatment by a multi-stacked rotatable plate assembly which is capable of solving the above-mentioned problems associated with the conventional types of air treatment systems.

DISCLOSURE OF INVENTION

This invention relates to treating air by a multi-stacked plate assembly having a multiplicity of circular plates stacked in a regularly spaced-apart manner so as to form a thin air layer between each adjacent pair of said circular plates, said circular plates provided on surfaces thereof with a function of decomposing foreign matter contained in the air, said circular plates rotated to cause said air layers to exhibit a self-blowing function, whereby air treatment by the decomposing function imparted to the plate surfaces is promoted.

This invention relates also to a process for treating air by a multi-stacked plate assembly having a multiplicity of circular plates stacked in a regularly spaced-apart manner so as to form a thin air layer between each adjacent pair of said circular plates, said circular plates provided on surfaces thereof with a function of removing foreign matter from the air, said circular plates rotated to cause said air layers to exhibit a self-blowing function, whereby air treatment by the removing function imparted to the plate surfaces is promoted.

This invention relates further to a process for treating air by a multi-stacked plate assembly having a multiplicity of circular plates stacked in a regularly spaced-apart manner so as to form a thin air layer between each adjacent pair of said circular plates, said circular plates provided on surfaces thereof with a function of releasing a fragrance, said circular plates rotated to cause said air layers to exhibit a self-blowing function, whereby air treatment by the fragrance-releasing function imparted to the plate surfaces is promoted.

The functions of treating air which are applied to plate surfaces as described above include, for example, the following:

(a) The spacing $\delta$ between each adjacent pair of said stacked circular plates has a value represented by the following expression:

$$0.05 < \frac{\delta}{d_0 \cdot n \cdot (\tau \cdot D_{AB})^{\frac{1}{2}}} < 1.5 \ (s/m)$$

wherein
$D_{AB}$ = diffusion coefficient of foreign matter (m²/s)
$\tau$ = dwell time of air under treatment between circular plates = (volume of air in plate assembly)/(flow rate of air through plate assembly) (s)
$d_0$ = outside diameter of circular plates (m)
n = rotational frequency (1/s or rps)
$\delta$ = spacing between adjacent circular plates (m)

(b) The function of decomposing foreign matter contained in air is imparted to said plate surfaces by a catalyst and/or an adsorbent supported on said circular plates.

(c) The function of removing foreign matter from air is imparted to said plate surfaces by a catalyst and/or an adsorbent supported on said circular plates.

(d) The function of decomposing foreign matter contained in air is imparted to said plate surfaces by a catalyst and/or an adsorbent constituting said circular plates.

(e) The function of removing foreign matter from air is imparted to said plate surfaces by a catalyst and/or an adsorbent constituting said circular plates.

(f) The function of removing foreign matter from air is imparted to said plate surfaces by a drying agent supported on said circular plates.

(g) The function of treating air is imparted to said plate surfaces by a drying agent constituting said circular plates.

(h) The function of treating air is imparted to said plate surfaces by a fragrant agent supported on said circular plates.

(i) The function of treating air is imparted to said plate surfaces by a fragrant agent constituting said circular plates.

(j) The function of treating air is imparted to said plate surfaces by deodorants which are supported respectively on said circular plates and which comprise catalysts and/or adsorbents capable of eliminating different kinds of odors, respectively.

(k) The function of treating air is imparted to said plate surfaces by deodorants which constitute said circular plates, respectively, and which comprise catalysts or adsorbents capable of eliminating different kinds of odors, respectively.

(l) The function of treating air is imparted to said plate surfaces by fragrant agents which are supported respectively on said circular plates and which are capable of releasing different kinds of fragrances, respectively.

(m) The function of treating air is imparted to said plate surface by fragrant agents which constitute said circular plates, respectively, and which are capable of releasing different kinds of fragrances, respectively.

(n) The function of treating air is imparted to said plate surfaces by use of a combination of at least two catalysts, at least two adsorbents, at least two drying agents, and at least two fragrant agents.

(o) A heater is disposed in proximity to said circular plates stacked in multi-layered form. (p) The function of treating air is imparted to one surface of each said circular plate.

(q) The function of treating air is imparted to both surfaces of each said circular plate, so that the function of treating air is possessed by both plate surfaces faced to each other through said thin air layer therebetween.

(r) Said circular plates comprise metal.

(s) Said circular plates comprise an inorganic or organic nonwoven fabric.

(t) Said circular plates comprise an inorganic or organic fibrous material.

(u) Said circular plates comprise an inorganic or organic porous material.

(v) A multiplicity of vanes ar interposed between said circular plates in a circumferentially regularly spaced-apart manner.

(w) The outer end of each said vane is located at a predetermined distance radially inward from the outer circumferential edge of said circular plate.

The term "circular plate" used herein means a plate the shape of which is a true circle, a partly cutaway circle, a polygon close in shape to a circle, a nearly circular shape, or the like. In addition, the term "regular(ly)" used with respect to the circular plate spacing $\delta$ not only refers to the case where the spacings $\delta$ between the circular plates are exactly equal to each other but also refers to the case where the spacings $\delta$ are different.

In this invention, a multiplicity of these circular plates are stacked with a gap between plates so as to form a thin layer of air within the gap.

When the stacked circular plates are rotated, each thin layer of air is pulled by shearing forces between circular plate and air, and a centrifugal force is exerted on the air layer, resulting in a self-blowing function.

Where the plate spacing in the multi-stacked plate assembly is reduced for increasing the area for contact of air with the functional member such as an agent for decomposition or removal of foreign matter from air, a fragrance-adding agent, etc. in order to enhance the air-treating function, the result is not an increased resistance to air flow but is an increase in the self-blowing function of the circular plates and an increase in the volume of air blown, as contrasted to the cases of sirocco fans or axial fans. The increase in the quantity of air blown leads to an increased air flow velocity between the circular plates, which together with the increased contact area ensures a marked improvement in the air-treating function, as compared to that according to the prior art.

In the general honeycomb-shaped air treatment systems, air flows through passages as a laminar flow and, therefore, the rate-determining step in the process of the air treating function is the diffusion (molecular diffusion) caused by a difference in concentration of foreign matter. In addition to the above synergistic effect of the increased air flow velocity and increased contact area, this invention utilizes new physical phenomena which, peculiar to plate fans, are generated by rotation of the stacked circular plates together with the thin air layers formed between the circular plates. Due to the effects of the new physical phenomena, the process of air treatment is no longer rate-determined by the molecular diffusion. Consequently, it has become possible, according to this invention, to achieve a further greater improvement in air-treating function as compared with the prior art.

More specifically, it has been found that the improvement of air treatment by the new physical phenomena is greater as the plate spacing $\delta$ (or the thickness of thin air layer) is smaller and as the circumferential velocity $\pi d_0 n$ at the outside diameter of the circular plates is greater. It has also been found that the improvement by the new physical phenomena is greater as the dwell time $\tau$ of air under treatment in its passage between the circular plates is longer and as the diffusion coefficient $D_{AB}$ of foreign matter flowing in the thin air layer is higher.

A preferable plate spacing $\delta$ (or preferable thickness of thin air layer) can be determined, on the one hand, theoretically from diffusion equations for fluids and, on the other hand, empirically by experiments on the relationships of actual circular plate outside diameter $d_0$, plate with spacing $\delta$, fan rotational frequency n, dwell time $\tau$, and diffusion coefficient of foreign matter $D_{AB}$.

FIG. 5 shows experimental results obtained by actually rotating a stack of circular plates with a thin air layer formed between the circular plates.

It was found that the air treatment performance is lowered rapidly when the value of $\delta/(d_0 \cdot n \cdot (\tau \cdot D_{AB})^{\frac{1}{2}})$, as described below, is increased beyond 1.5 (s/m). It was also found that when the value of $\delta/(d_0 \cdot n \cdot (\tau \cdot D_{AB})^{\frac{1}{2}})$ is decreased below 0.05 (s/m), an extremely large drop in the flow rate of air is caused even under fan rotation, and the air treatment function is again lowered rapidly. Thus, it was found that a stable and highly efficient air-treating function can be obtained with the value of $\delta/(d_0 \cdot n \cdot (\tau \cdot D_{AB})^{\frac{1}{2}})$ in the range from 0.05 to 1.5 s/m).

$$0.05 < \frac{\delta}{d_0 \cdot n \cdot (\tau \cdot D_{AB})^{\frac{1}{2}}} < 1.5 \text{ (s/m)}$$

wherein
 $D_{AB}$ = diffusion coefficient of foreign matter (m²/s)
 $\tau$ = dwell time of air under treatment between circular plates = (volume of air in plate assembly)/(flow rate of air through plate assembly) (s)
 $d_0$ = outside diameter of circular plates (m)
 n = rotational frequency (1/s or rps)
 $\delta$ = spacing between adjacent circular plates (m)

The term $(\tau \cdot D_{AB})^{\frac{1}{2}}$ in the formula $\delta/(d_0 \cdot n \cdot (\tau \cdot D_{AB})^{\frac{1}{2}})$ represents the effect of molecular diffusion, whereas the term $d_0 \cdot n$ represents the effects of the new physical phenomena peculiar to the plate fan generated by the rotation of thin air layers.

The physical phenomena peculiar to the plate fans include such phenomena as separation of laminar flow, promoted turbulence of boundary layers near the plate surfaces, and propagating stall, which will be explained below.

The separation of laminar flow means the separation of boundary layers, at which a laminar air flow passing between circular plates makes contact with the plate surface, under the influence of a large reduction in the flow velocity of air near the plate surfaces due to a large pressure rise in the radial direction and to a large frictional loss on the plate surfaces, during the radially outward flow of air between the circular plates. The separation of laminar flow causes an activated contact of, for example, a substance supported on the plate surfaces with the air flow, thereby promoting the air-treating function.

The promoted turbulence of boundary layers near the plate surfaces refers to the turbulence of boundary layers between plate surface and air flow and the generation of turbulent diffusion, which are caused under the influence of surface roughness of the circular plates by an increased distance of plate-air contact and an increased velocity of air relative to the circular plate, which are in turn due to the logarithmic spiral path of air driven by the rotation of the circular plates to flow through the thin air layer from the central to the outer side of the circular plates. Such a promoted turbulence causes an activated contact of air with an air-treating agent, thereby enhancing the air-treating function.

The propagating stall means the generation of a disturbed pulsating flow of air between circular plates due to the rotation, in the same direction but at a lower speed in relation to the rotating circular plates, of a plurality of stalling cells of air which are produced in the thin air layer at regular intervals along the circumference of the circular plates when the flow rate of air through the plate assembly is low. This phenomenon, similarly to the separation of laminar flow and the promoted turbulence of boundary layers near plate surfaces, activates the contact between the substance supported on the plate surfaces and the air flow and also activates diffusion, thereby promoting the air-treating function.

Accordingly, where a catalyst, drying agent, deodorant or the like is supported on the surfaces of the rotating circular plates, the aforesaid separation of laminar flow, the promoted turbulence of boundary layers near plate surfaces, the propagating stall and the like generated in thin air layers by the rotation of the circular plates enhance the air-treating function, and enable each particular air treatment system to fully display the intended air-treating function.

In addition, because the rotation of circular plates in the plate fan as above causes air to make contact with the circular plate over a long distance and to flow along a logarithmic spiral path, a steady drift with respect to the circumferential direction is hardly generated, even if the plate spacing is nonuniform. Therefore, the entire surface area of the circular plates can be utilized effectively, which also contributes to an augmented air-treating function.

Furthermore, since the plate fan according to this invention has circular plates stacked in a multi-layered form, different air-treating functions can be applied to different circular plates, or to both surfaces of each circular plate or even to the same surface of each circular plate.

Accordingly, a plurality of kinds of air treatments for decomposition or removal of foreign matter or for imparting fragrance can be accomplished with a single system.

Where an air-treating function is provided on only one side surface of each circular plate in the plate fan, there would occur the problem of, for example, deposition of malodorous or other foreign matter on the nonfunctional side of each circular plate and, further, accumulation of the foreign matter in an undecomposed state. If such a condition continues for a long time, the air treatment system would release the malodorous or other foreign matter together with the treated air, contrary to the intended operation of the system, so that the inherent air-treating function of the system would be lowered.

Where an air-treating function is provided on both surfaces of each circular plate, on the other hand, the situation mentioned just above does not occur; namely, malodorous foreign matter is decomposed effectively between the circular plates of the plate fan, and a stable air treatment performance can be maintained for a long time.

Besides, where air to be treated is heated by a heater disposed on the upstream side of and in proximity to an inlet of the plate fan, catalytic decomposition reaction or release of fragrance (fragrant agent) is accelerated and, further, it is possible to achieve regeneration of a catalyst, adsorbent, drying agent or the like.

Also, where a plurality of vanes are arranged in the thin air layer in a circumferentially spaced-apart manner, a blowing function based on vane work is obtained in addition to the blowing function based on the shearing force generated at the plate surfaces by rotation of the circular plates. This leads to an additional increase in the volume of air blown.

In such a construction, a vortex is generated behind each vane and the velocity distribution of air discharged from the outer circumferential edges of the circular plates is distorted greatly, resulting in generation of noise. Taking this problem into account, this invention provides a construction wherein the radially outer ends of the vanes are located on the inner side of the outer circumferential edges of the circular plates, so as to prevent the generation and development of vortexes, to thereby suppress turbulent-flow noise and to make uniform the velocity distribution of air being discharged. Thus, the generation of noise by interference of air with a tongue portion of a fan casing, arising from distorted air velocity, and the generation of noise due to turbulent flow can be prevented, and a quieter operation can be ensured.

BRIEF DESCRIPTION OF DRAWINGS

FIG. 10a: A sectional view of an area of FIG. 10 at lines 10a, 10a, showing plate spacing.

FIG. 13: A partly cutaway front view of an important part of an ozone deodorizing system according to a further modification.

FIG. 13a: A sectional view of an area of FIG. 13 at lines 13a, 13a, showing plate spacing.

BEST MODE FOR CARRYING OUT THE INVENTION

The best modes for carrying out this invention will now be explained in detail below, with reference to some embodiments of the invention as shown in the attached drawings.

Embodiment 1

Figure 1:
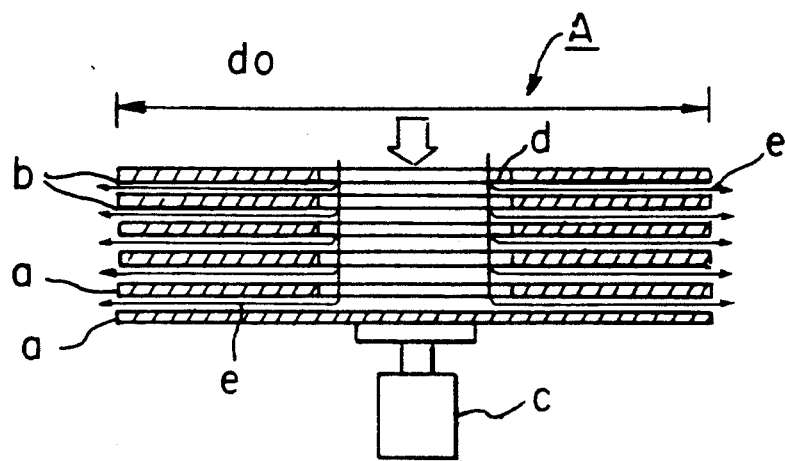
FIG. 1: A conceptual illustration of the basic construction of a multi-stacked plate fan for use in a process for air treatment by multi-stacked plate assembly according to Embodiment 1 of this invention.
Figure 2:
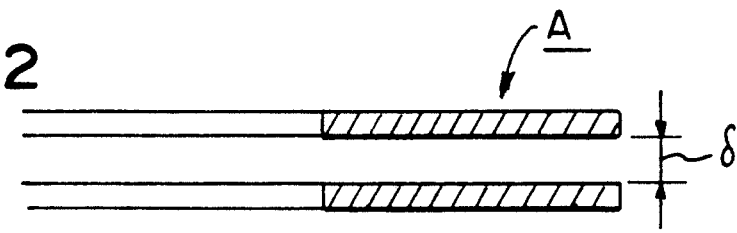
FIG. 2: An enlarged view of an important part of the circular plates of the multi-stacked plate fan.
Figure 3:
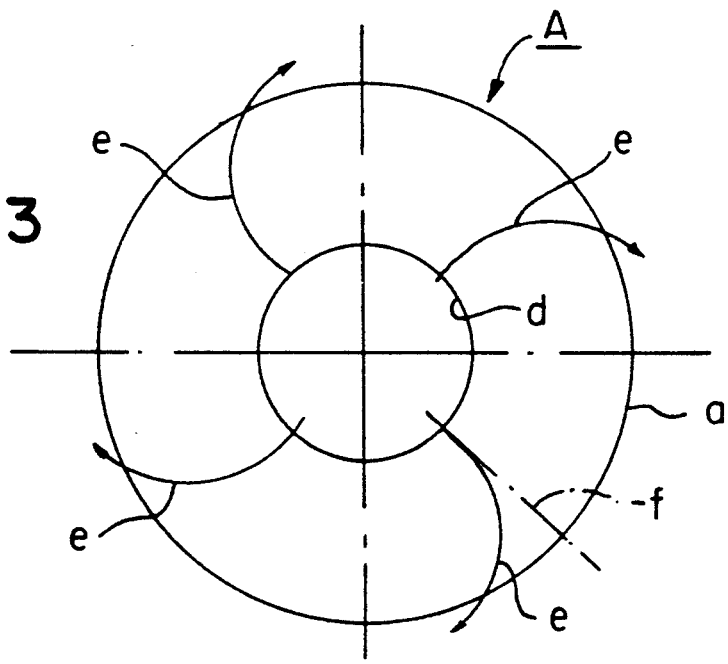
FIG. 3: A plan view of the multi-stacked plate fan.

This embodiment relates to the basic construction of an apparatus for carrying out air treatment by a multi-stacked plate assembly constituting the gist of this invention, the apparatus being presented as a multi-stacked plate fan as shown in FIGS. 1 to 3.

As shown in FIGS. 1 to 3, a multi-stacked plate fan A constituting the basic construction comprises circular plates "a" stacked in a multi-layer form with regular spacings $\delta$ therebetween so that a thin air layer b is formed between each pair of adjacent circular plates "a", "a", and the stack of circular plates "a" is connected, for rotation, to an output shaft of a motor c at a central portion of the lowermost circular plate. The term "circular plate" used herein includes plates the shape of which is a true circle, a partly cutaway circle, a polygon resembling a circle, a nearly circular shape or the like. The "regular spacings $\delta$" refers not only to the case where the spacings $\delta$ are equal to each other but also to the case where the spacings $\delta$ are not equal.

All of the circular plates "a" except the lowermost circular plate "a" are annular circular plates, and the uppermost circular plate "a" is provided with an air inlet opening d in a central portion thereof.

When the circular plates "a" are rotated, therefore, the thin air layer b receives a centrifugal force exerted thereon due to shearing forces acting between the air layer b and the circular plate a. The centrifugal force gives rise to a self-blowing function, so that, as shown in FIG. 3, an air flow e enters through the air inlet opening d into each thin air layer b, passes through the layer b, and then goes out via the outer circumferential edges of the circular plates "a" to the exterior.

Either one or both side surfaces of each circular plate a are treated as described below, for decomposition or removal of foreign matter contained in air or for adding a fragrance to air.

The treatment may be carried out by supporting a catalyst, adsorbent, drying agent, fragrant agent, deodorant or the like on the circular plates "a", or by forming the circular plates "a" themselves from a catalyst, adsorbent, drying agent, fragrant agent, deodorant or the like.

By the term "supporting" herein is meant adhesion to the plate surfaces, infiltration into the material constituting the circular plates, and other similar processes.

Materials which can be used for the circular plates include, for example, fibrous materials such as rock wool, slag wool, glass fibers, silica fibers, alumina fibers, mullite fibers, ceramic fibers, zirconia fibers, etc.; porous materials consisting of or based on ceramic, resin, aluminum or the like; metallic materials; nonwoven fabrics, and so on.

In the present embodiment, a copper-ascorbic acid deodorant used in air cleaners, air conditioners, etc. was used. The deodorant was obtained by mixing and dispersing cuprous oxide and a porous powder of active carbon, zeolite or the like into an aqueous solution of L-ascorbic acid (which is a preventive against oxidative deterioration of cuprous oxide) to form a mixture, then adding thereto an organic binder such as an acrylic emulsion binder or an inorganic binder such as colloidal silica, for fixing the cuprous oxide and porous powder, to thereby prepare a slurry, and impregnating a synthetic paper made from ceramic fibers with the slurry. The resultant material was blanked into annular shape with 75 mm outside diameter and 32 mm inside diameter, to obtain 0.5-mm thick circular plates "a". Four sets of the circular plates "a" thus obtained were stacked to have equal plate spacings of 0.5 mm, 1 mm, 3 mm, and 5 mm, respectively, with a thin air layer b between each pair of adjacent circular plates "a", a to assemble four kinds of multi-stacked plate fans A.

When the motor c for the multi-stacked plate fan A is driven, each circular plate "a" is rotated, whereby shearing forces are generated between circular plate a and thin air layer b. Due to the shearing forces, the thin air layers b are rotated in the manner of being pulled by the circular plates "a". The rotation of the thin air layer b produces a centrifugal force in the air layer b, thereby offering a self-blowing function.

While each of the four kinds of multi-stacked plate fans A differing in plate spacing $\delta$ was rotated, $H_2S$ assumed to be foreign matter contained in air is introduced continuously via the intake port of the plate fan A under the conditions of an air temperature of 20° C. and a humidity of 60% RH so as to have a $H_2S$ concentration of 5 ppm at the intake port. After 30 minutes, the concentration of $H_2S$ in the exhaust gas was measured by gas chromatography (detector: FID or PPD) to determine odor removal ratio.

The results of measurements under various conditions are summarized in Table 1 below.

In addition, the value of calculated plate spacing h based on molecular diffusion, obtained by modifying a diffusion equation, and the value of relational formula $\delta/(d_0 \cdot n \cdot (\tau \cdot D_{AB})^{\frac{1}{2}})$, used for specifying the actual plate spacing $\delta$, were also calculated, wherein $$h = 2(\tau \cdot D_{AB}/\pi)^{\frac{1}{2}}$$

$D_{AB}$ = diffusion coefficient of foreign matter (m²/s)
$\tau$ = dwell time of air under treatment between circular plates = (volume of air in plate assembly)/(flow rate of air through plate assembly) (s)
$d_0$ = outside diameter of circular plates (m)
$n$ = rotational frequency (1/s or rps)

TABLE 1

| Plate spacing (m) | Rotational frequency (rps) | Air flow rate (l/m) | $\delta/h$ | $\dfrac{\delta}{d_0 \cdot n \cdot (\tau \cdot D_{AB})^{\frac{1}{2}}}$ | removal ratio (%) |
|---|---|---|---|---|---|
| 0.1 | —* | —* | —* | —* | —* |
| 0.5 | 2140 | 100 | 0.7 | 0.30 | 100 |
| 1.0 | 2145 | 73 | 1.2 | 0.51 | 100 |
| 3.0 | 1800 | 50 | 1.7 | 0.87 | 100 |
| 5.0 | 1800 | 30 | 2.3 | 1.10 | 92 |

*Was not measurable.

Figure 4:
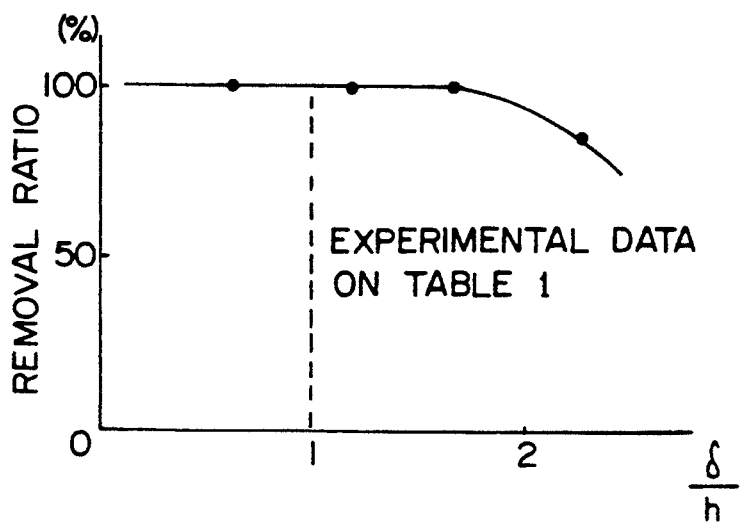
FIG. 4: A graph showing the relationship between the ratio $\delta/h$ of an actual plate spacing $\delta$ to a preferable thin air layer thickness h based on a diffusion equation, etc., and the foreign matter removal ratio.

As is clear from the results given in Table 1 above, with particular reference to the relationship between the ratio $\delta/h$, of the calculated plate spacing h based on molecular diffusion obtained by modifying a diffusion equation to the actual plate spacing $\delta$, and the odor removal ratio, it was found that a high removal ratio is naturally obtained at $\delta/h = 0.7$ in FIG. 4 and a similar high removal ratio can also be obtained at $\delta/h = 1.2$ and at $\delta/h = 1.7$.

As is shown by comparison of the experimental data for a plate spacing of 0.5 mm in Table 1 with that for a plate spacing of 1 mm and by comparison of the experimental data for a plate spacing of 3 mm with that for a plate spacing of 5 mm, the quantity of air blown is increased as the plate spacing $\delta$ is reduced while the circular plate rotational frequency is kept constant. Also, a comparison of the experimental data for a plate spacing of 3 mm and that for a plate spacing of 5 mm shows an improvement in treatment performance, attending on the increase in the quantity of air blown. Thus it is seen that a reduction in the plate spacing $\delta$ augments the self-blowing function, thereby promising an increased air flow rate. It is also seen that the air-treating function is promoted by a synergistic effect of the increased flow velocity of air between circular plates "a", "a", which arises from the increased air flow rate, and the increased area of contact between air and the functional material.

Figure 6:
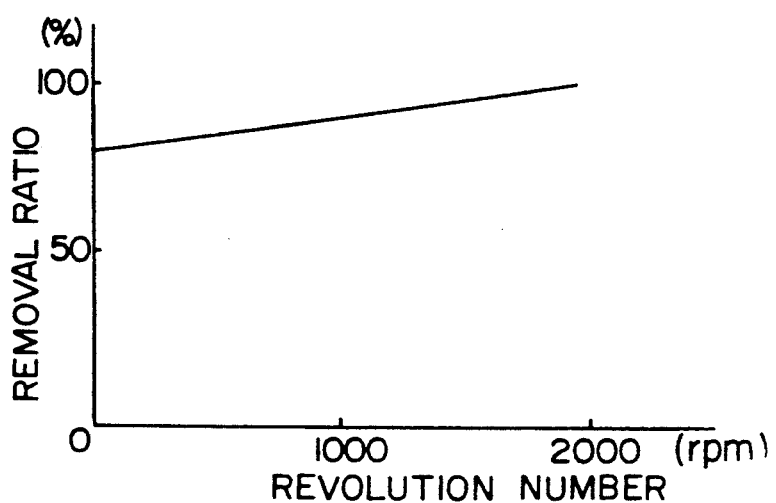
FIG. 6: A graph showing the relationship between the rotational frequency of the multi-stacked plate fan and the foreign matter removal ratio.

As a result of another experiment carried out at a fixed air flow rate of 100l/min by using the multi-stacked plate fan A with a plate spacing of 0.5 mm under the aforementioned conditions, it was found that the removal ratio increases with increasing rotational frequency, as shown in FIG. 6. These findings indicate that in the multi-stacked plate fans A comprising the thin air layers b, the air-treating function is promoted not only by the diffusion driven by concentration differentials usually generated in the cases of ordinary honeycomb-shaped deodorant but also by the turbulent diffusion caused by special physical phenomena such as separation of laminar flow, promoted turbulence of boundary layers near plate surfaces, propagating stall, etc. which are peculiar to the thin air layers b.

Because of the separation of laminar flow, the boundary layers at which the laminar air flow e passing through the thin air layer b between the circular plates "a", a makes contact with the surface of the circular plate a are separated from the plate surface, whereby the contact of, for example, a deodorant supported on the surface of the circular plate "a" with the air flow is activated, resulting in deodorizing the air.

In addition, because the rotation of the circular plates "a" causes air to flow through the thin air layer b along a logarithmic spiral path from the central to the outer circumferential edge of the circular plate "a", the distance of contact of the circular plate "a" and air is elongated and the velocity of air relative to the circular plate "a" is increased. Under the influence of the surface roughness of the circular plates "a", therefore, the boundary layer between the surface of the circular plate "a" and air is disturbed, to generate turbulent diffusion, or promote turbulence near the surface of the circular plate "a". The turbulence promoted activates the contact between the air flow and the deodorant, resulting in a further promotion of the deodorizing function.

Where the air flow rate through the multi-stacked plate fan A is low, a plurality of stalling cells of air appear in each thin air layer b at regular intervals along the circumference of the circular plate "a", and rotate in the same direction as the circular plates "a" but at a lower rate, whereby a disturbed pulsating flow is generated in the thin air layer b. That is, propagating stall is brought about. The propagating stall, similarly to the separation of laminar flow and the promoted turbulence near the surfaces of the circular plate "a", activates the contact of the deodorant supported on the surface of the circular plate "a" with the air flow and also activates diffusion, thereby promoting the deodorizing function.

Thus, where a deodorant is supported on the surfaces of the rotating circular plates "a", the above-mentioned phenomena generated in the thin air layers b by rotation of the circular plates "a", such as the separation of laminar flow, the promoted turbulence near the surfaces of the circular plates "a", the propagating stall, etc. produce a remarkable deodorizing effect.

Figure 5:
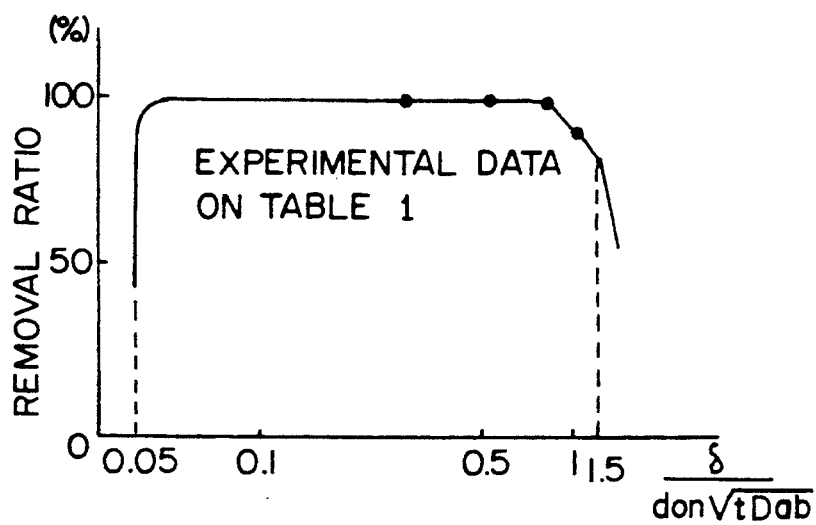
FIG. 5: A graph showing the relationship between $\delta/(d_0 n(\tau D_{AB})^{\frac{1}{2}})$ derived from the actual plate spacing $\delta$ by compensation for molecular diffusion as well as turbulent diffusion, and the foreign matter removal ratio.

Calculated values of the relational formula $\delta/(d_0 \cdot n \cdot (\tau \cdot D_{AB})^{\frac{1}{2}})$, which is based on considerations of the outer circumferential velocity $nd_0$ of the circular plate "a" representing the influence of the promotion of air-treating function by turbulent diffusion and another parameter $(\tau \cdot D_{AB})^{1/78}$ representing the influence of the diffusion due to concentration distribution, are also shown in Table 1 above. For all of the four kinds of multi-stacked plate fans, the value of the relational formula is in the range of $0.05 < \delta/(d_0 \cdot n \cdot (\tau \cdot D_{AB})^{\frac{1}{2}}) < 1.5$ (s/m), which indicates that the plate spacing $\delta$ in each case is in a preferable range. In fact, a high removal ratio was obtained in each of the four cases, as is clearly seen from Table 1 above or FIG. 5.

Naturally, other substances than the above-mentioned deodorant, for example, catalysts, adsorbents, etc. usable for other applications, such as drying agents, can also be supported on the circular plates "a" and can similarly accomplish satisfactorily the respective air-treating functions intended.

As shown in FIG. 3, furthermore, in the present embodiment the rotation of the circular plates "a" causes the length of an air flow e on the circular plate "a", or the distance of contact of circular plate "a" with air, to be considerably greater than that of an air flow f without rotation of the circular plates "a". The rotation of the circular plates "a" also increases the relative velocity of air with respect to the circular plate "a", and causes air to flow along a path resembling a logarithmic spiral. Therefore, even where the spacing $\delta$ between the circular plates "a", a is not uniform, a steady drift with respect to the circumferential direction is hardly generated, and an increased air-treating function is ensured.

The copper-ascorbic acid deodorant used in the present embodiment is capable of decomposing sulfur-containing odorous substances through oxidation by the oxidizing power of cuprous salt, thereby achieving deodorization. Therefore, the deodorization can be accomplished only by bringing the deodorant into contact with the sulfur-containing malodors. Besides, the reducing power of L-ascorbic acid suppresses the oxidation of univalent copper and regenerates a cupric salt (Which is a product of oxidative deactivation) into a cuprous salt, so that the useful life of the deodorant can be maintained for a long time.

Embodiment 2

The multi-stacked plate fan A constructed as described above can be used for an ozone deodorizing system. One embodiment in which the fan A is incorporated in a toilet stool body will now be explained in detail below, with reference to FIGS. 7 to 10a.

Figure 7:
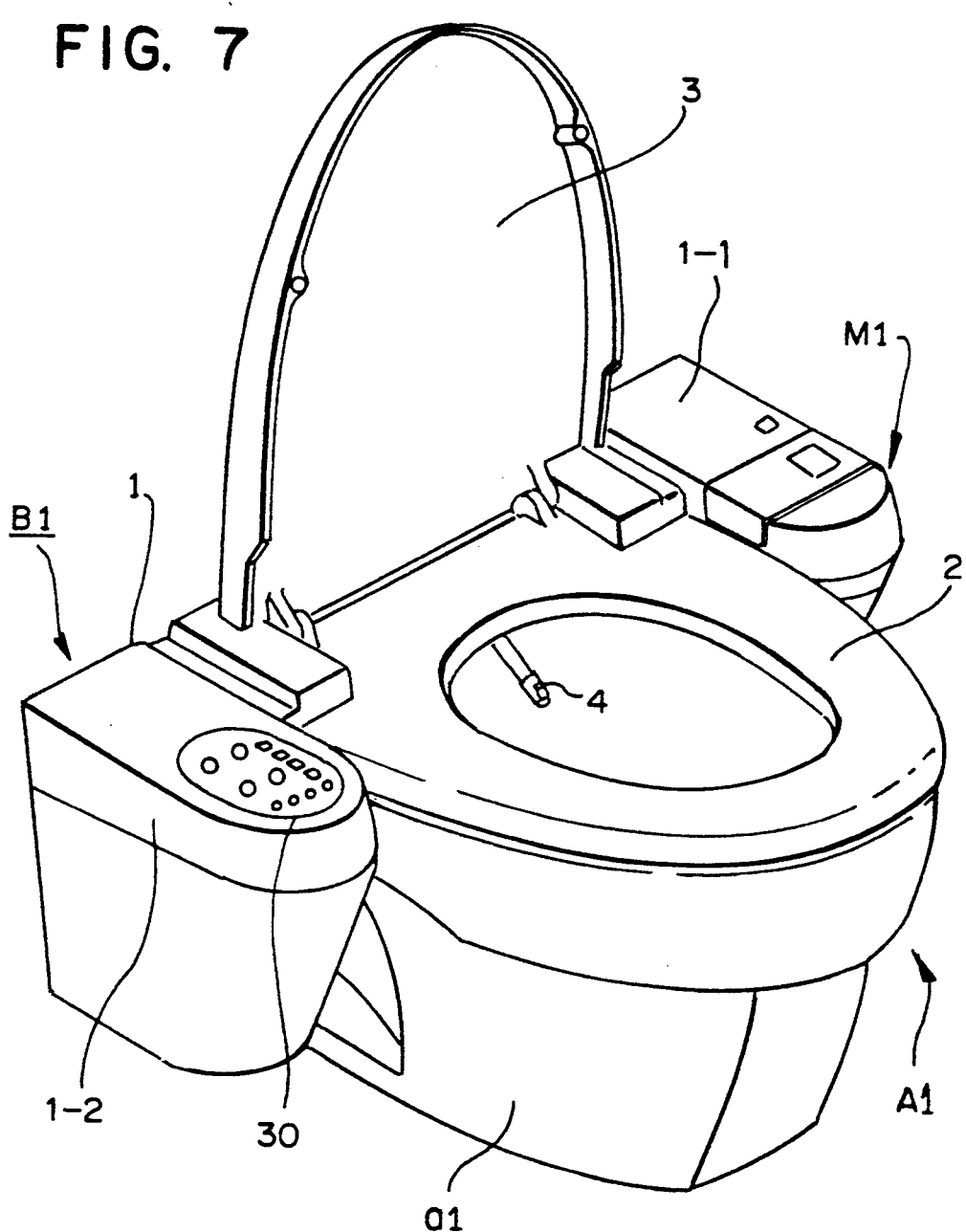
FIG. 7: A total perspective view of a toilet stool equipped with a deodorizing system comprising a multi-stacked plate fan according to Embodiment 2.
Figure 8:
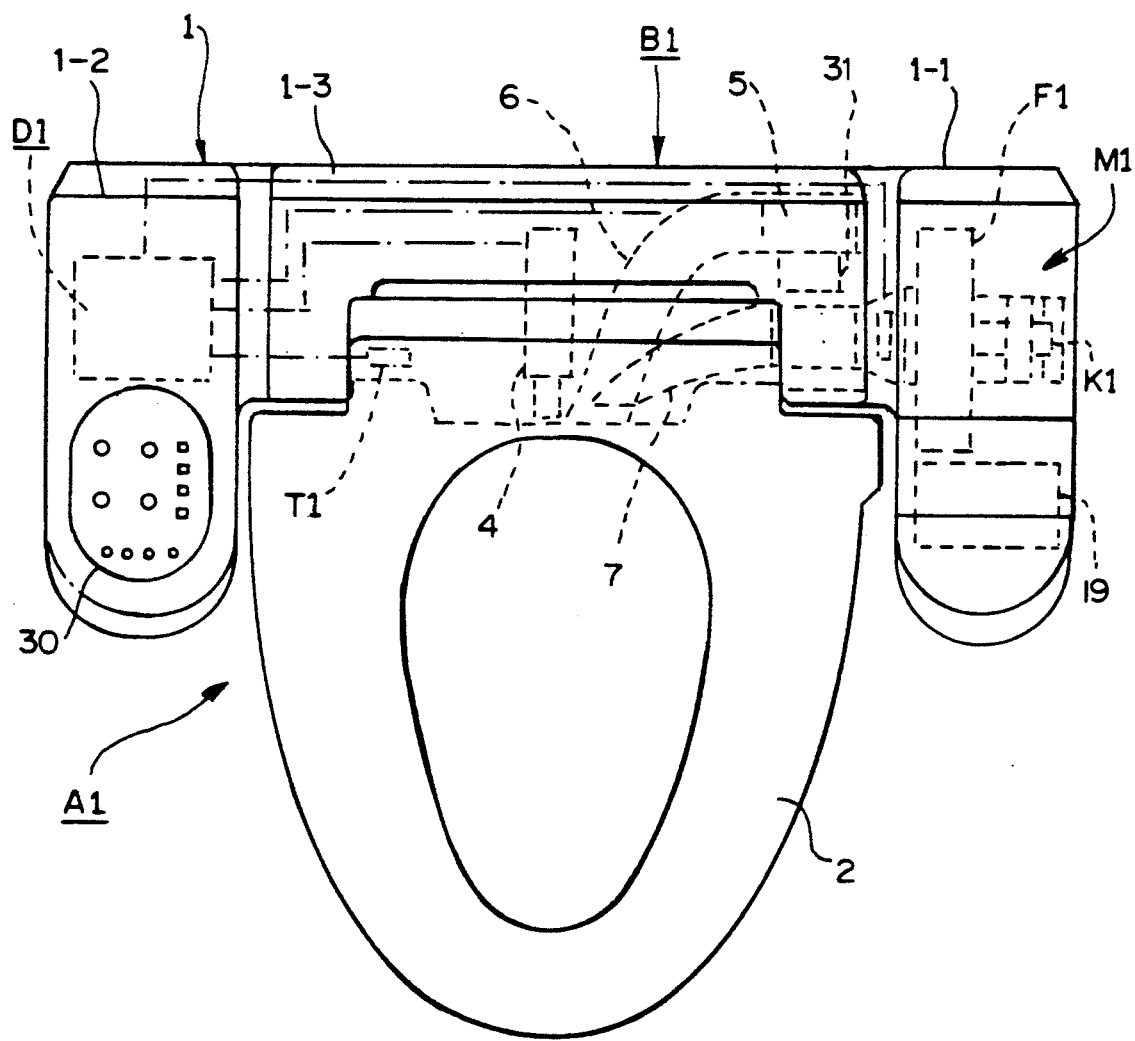
FIG. 8: A total plan view of the toilet stool.

Referring to FIGS. 7 and 8, there is shown the total construction of a toilet stool body A1 incorporating an ozone deodorizing system M1 equipped with a deodorizer fan according to this invention.

As shown in the figures, the toilet stool body A1 comprises a sanitary washing system B1 for washing the private parts, which is arranged astride an upper surface of a rear portion of the stool body A1. The sanitary washing system B1 has a functional block casing 1, which comprises a toilet seat 2 and an openable lid 3. In the functional block casing 1 are disposed a hot water tank, a valve unit and the like for supplying hot water for washing the private parts. Also arranged inside the casing 1 is a nozzle 4 for washing the private parts, which is protruded into and retracted from a bowl portion a1 of the stool body A1.

In addition to the private part washing function, the functional block casing 1 is provided with a hot-air fan 5 and a hot-air duct 6 for drying, as described below. Further, a deodorization duct 7 is provided in the vicinity of the hot-air duct 6. As shown in FIG. 8, the deodorization duct 7 is extended into a functional block casing 1-1 at the left end, to communicate with the ozone deodorizing system M1, which will be described below.

Figure 9:
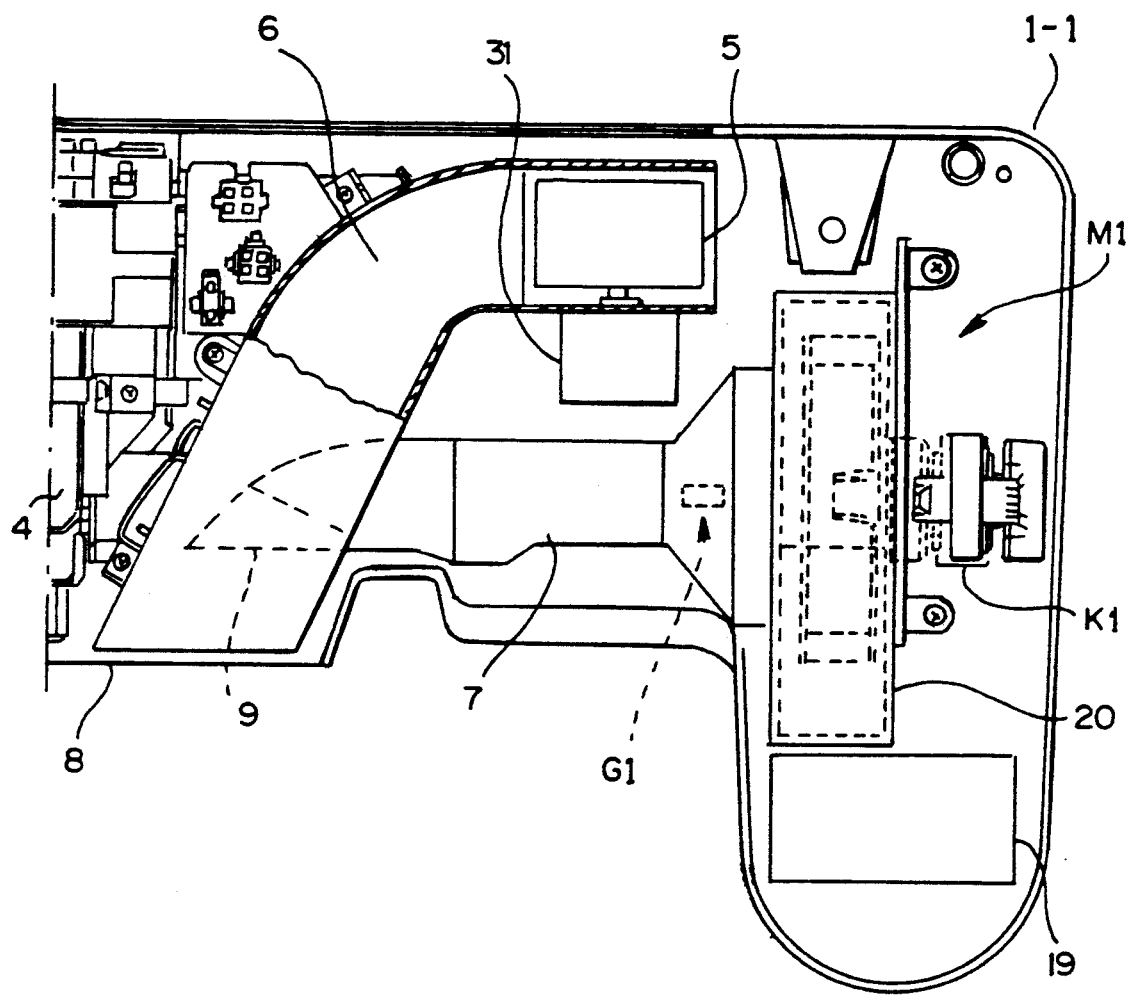
FIG. 9: A partly cutaway plan view of an important part of a main body of the toilet stool.
Figure 10:
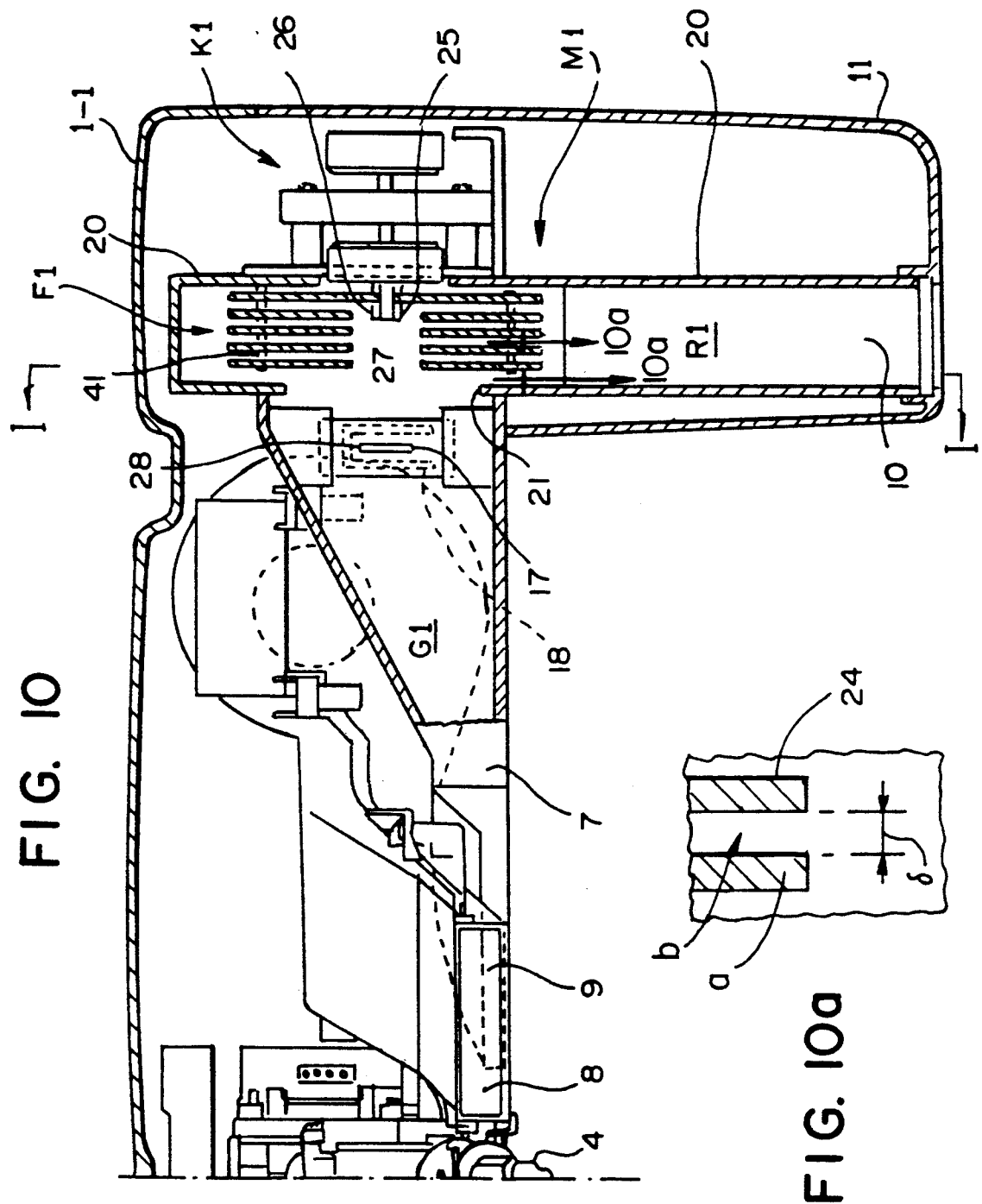
FIG. 10: A partly cutaway plan view of an important part of an ozone deodorizing system.

In the total construction as above, the hot-air fan 5 and hot-air duct 6 constituting an hot-air drying system will be first described, with reference to FIGS. 9 and 10. The hot-air fan 5 is disposed in an upper part of a left wing portion 1-1 of the functional block casing 1, and the hot-air duct 6 is extended from the fan 5 through an upper part of an intermediate portion 1-3 of the casing 1, to have a hot-air outlet port 8 opened at a location deviated slightly leftward from a central part of the intermediate portion 1-3 of the casing 1. Denoted by 1-2 is a right wing portion of the functional block casing 1, for enclosing therein a functional block of the private part washing system.

On the lower side of the hot-air duct 6 is disposed the deodorization duct 7, as shown in FIG. 10. The duct 7 has, at its front end, an intake port 9 opened into the bowl portion a1 of the stool body A1, and extends from the intake port 9 along the intermediate portion 1-3 of the casing 1 to a central part of the left wing portion 1-1. The duct 7 communicates, at its terminal end, with an ozone treatment passage R1 formed in the ozone deodorizing system M1.

The ozone treatment passage R1 of the ozone deodorizing system M1 is formed at its terminal end with an exhaust port 10, as shown in FIG. 10. The exhaust port 10 is opened at the bottom end of a downwardly extending chamber casing 11 formed at the left wing portion 1-3 of the functional block casing 1.

Thus, the deodorizing passage for removing malodors generated in the toilet stool body A1 is formed along the whole course from the intake port 9 of the deodorization duct 7 to the exhaust port 10 of the ozone treatment passage R1, with the ozone deodorizing system M1 intermediately disposed in the course.

The ozone deodorizing system M1 as above is in this embodiment, enclosed in the chamber casing 11 substantially completely except for an ozone generating block G1.

The construction of the ozone deodorizing system M1 will now be explained below, with reference to FIGS. 7 to 12. As shown in FIGS. 9 and 10, the ozone generating block G1 constituting part of the ozone deodorizing system M1 is disposed in a central area within a rear portion of the deodorization duct 7.

In this embodiment, the ozone generating block G1 comprises an ozonizer 17 having a discharge electrode 28 on one side of a base plate 27, and a heater 18 fastened to the other side of the base plate 27. The base plate 27 is disposed in the deodorization duct 7, in parallel to the axial direction of the deodorizing passage and vertically.

The ozonizer 17 is connected to a high voltage generator 19 disposed in the chamber casing 11, and the generator 19 is connected to a control block D1. Based on an output from the control block D1 (FIG. 8), a high voltage is applied from the high voltage generator 19 to the ozonizer 17, whereby ozone can be generated in the deodorization duct 7. The heater 18 is provided for heating the ozonizer 17, thereby lowering the relative humidity of the atmosphere in the vicinity of the ozonizer 17, in order to promote the ozone generation by the ozonizer 17.

As shown in FIG. 10, the ozone treatment passage R1 provided in the chamber casing 11 is formed in a hollow casing 20 extending vertically. The ozone treatment passage R1 communicates at an upper portion thereof with the interior of the deodorization duct 7 through a communication port 21.

Figure 11:
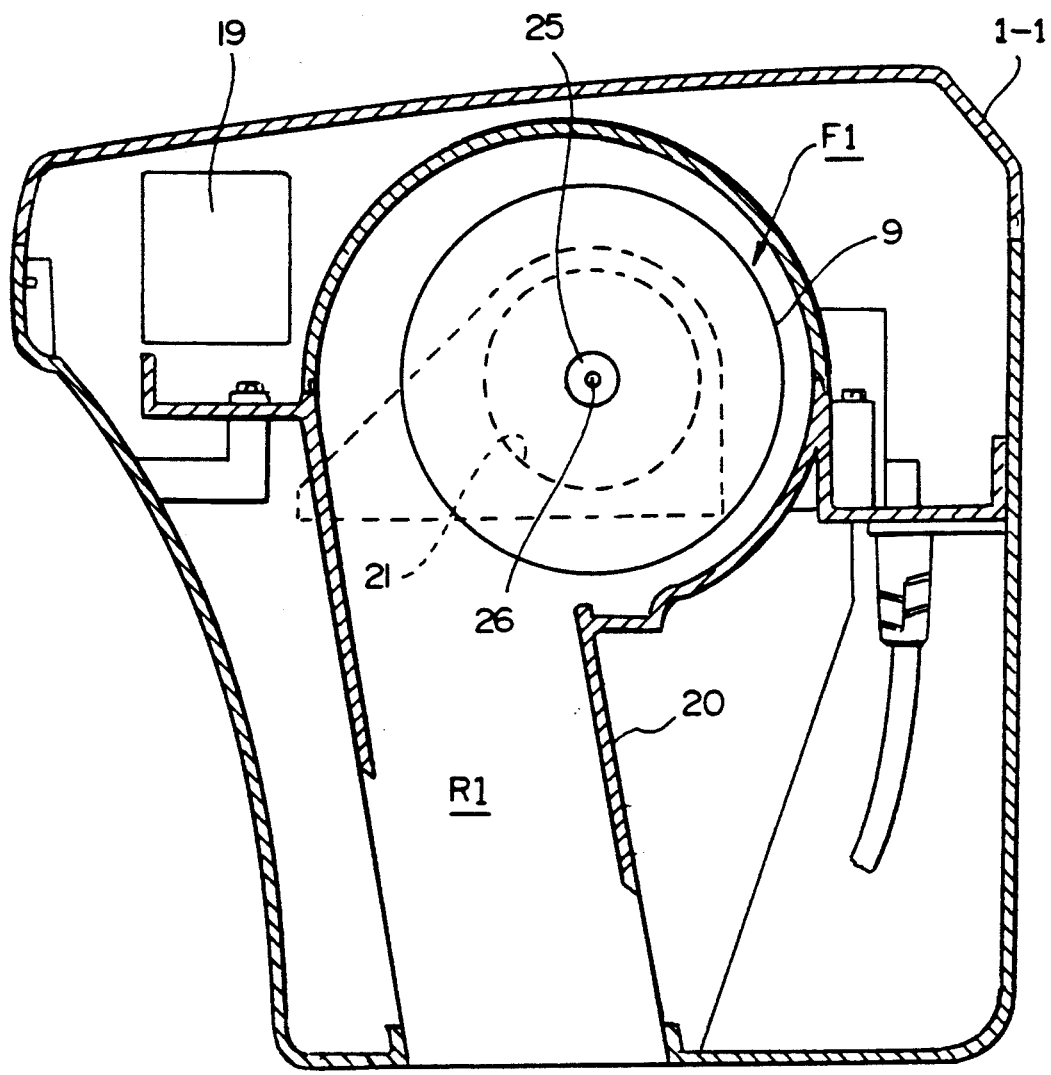
FIG. 11: A sectional view taken along line I—I of FIG. 10.

In the upper portion of the ozone treatment passage R1 on the downstream side of the ozone generating block G1, a deodorizer fan F1 is rotatably disposed, as shown in FIGS. 10 and 11. The deodorizer fan F1, in this embodiment, has a construction in which annular circular plates "a" formed of a catalyst are stacked at regular intervals in a multi-layer form, with spacers 41 interposed therebetween, and the stack is mounted on a boss portion 25.

The boss portion 25 of the deodorizer fan F1 is attached to an output shaft 26 of a rotating motor K1 disposed at a rear portion of the hollow casing 20. The deodorizer fan F1 is capable of sucking the malodorous air, generated in the toilet stool body A1, into the ozone treatment passage R1 via the deodorization duct 7, and is also capable of mixing effectively the ozone generated in the ozone generating block G1 with the malodorous air, as will be described below.

The catalyst forming the circular plates "a" of the deodorizer fan F1 serves to promote the decomposition of ozone into oxygen and active oxygen. Therefore, the deodorizing action is promoted positively and rapidly on the surfaces of each circular plate "a" formed of the catalyst, through the mixing of ozone with malodors.

As the catalyst, a variety of compositions can be used. For example, materials comprising a metal such as Mg, Ag, Fe, Co, Zn, Ni, Pt, Pd, Rn, etc. or an oxide thereof supported on a carrier such as alumina, silica-alumina, zirconia, diatomaceous earth, silica-titania, silica-zirconium, titania, zirconia, etc. may be formed into circular plates "a" so as to assemble the deodorizer fan F1 therefrom.

Other constituents than the above-described, in the embodiment as shown, will now be explained. Referring to FIGS. 7 and 8, numeral 30 denotes a console block, which comprises various operating switches necessary for a private part washing operation. In FIG. 9, denoted by 31 is a motor for driving the hot-air fan 5.

Now, deodorizing treatment, for removing malodors generated in the toilet stool body A1, by the ozone deodorizing system M1 having the above construction will be explained, with reference to FIGS. 10 and 11. First, when the user is seated on the seat 2 of the toilet stool equipped with the ozone deodorizing system, a seating sensor T1 disposed on the rear side of the seat 2 sends a detection output to the control block D1. The control block D1 produces driving outputs to drive the deodorizer fan F1 and to cause the high voltage generator 19 to generate a high voltage, which is applied to the ozonizer 17, whereby ozone is generated in the ozone treatment passage R1. As a result, the malodors generated in the interior of the stool body A1 are sucked into the ozone treatment passage R1, in which they are effectively mixed with the ozone, and a positive and rapid deodorizing treatment is carried out at the surfaces of each circular plate "a" (formed of the catalyst) of the deodorizer fan F1.

Taking hydrogen sulfide, methyl mercaptan, ammonia, etc. as examples of malodorous substances contained in air, the deodorizing treatment is considered to involve such reactions as follows:

$$H_2S + 3O_3 \rightarrow SO_2 + \ldots$$

$$CH_3SH + 3O_3 \rightarrow CH_3SO_3H + \ldots$$

$$NH_3 + 3O_3 \rightarrow HNO_3 + \ldots$$

Thus, the malodorous substances are decomposed by reaction with ozone into odorless components.

Thereafter, the exhaust air thus deodorized satisfactorily is discharged through the exhaust port 10 at the rear end of the hollow casing 20 into the toilet space.

In this embodiment, further, as shown in FIGS. 10, 10a, and 11, the deodorizer fan F1 is constructed by stacking the circular plates "a" formed of the catalyst in a multi-layered form and mounting the resulting stack on the boss portion 25.

In such a construction, when the motor K1 for the multi-stacked plate fan F1 is driven, each of the circular plates "a" is rotated to impart a self-blowing function to each thin air layer b. Due to the self-blowing function, separation of laminar flow, propagating stall, promoted turbulence near plate surfaces, etc. are caused in the thin air layers b, whereby the performance of the deodorizing treatment function is markedly enhanced and the treatment is promoted.

In this manner, where the rotating circular plates "a" are formed of a catalyst, it is possible to produce a remarkable deodorizing effect by the separation of laminar flow in the thin air layers b, the propagating stall, the promoted turbulence near the plate surfaces, and the like which are caused by the rotation of the circular plates "a" as described above.

Further, as has been described with reference to FIG. 3, in the present embodiment, also, the rotation of the circular plates "a" causes the length of an air flow e on the circular plate "a", or the distance of contact between circular plate and air, to be considerably greater than that of an air flow f without rotation of the circular plates "a". In addition, the rotation of the circular plates "a" ensures an increased relative velocity of air with respect to the circular plate "a", and causes air to flow along a path resembling a logarithmic spiral. Even where the plate spacing δ is not uniform, therefore, a steady drift with respect to the circumferential direction is generated, and the entire surface area of the circular plates "a" can be used effectively. This also contributes to an increase in the deodorizing treatment.

Particularly, because the deodorizer fan F1 comprises such circular plates "a" stacked in a multi-layered form, the self-blowing function prevents the flow rate of air from being lowered when the plate spacing δ is reduced. It is therefore possible to increase the number of the circular plates "a" with the effect of a marked increase in the area of contact between air and functional agent, thereby further augmenting the deodorizing treatment.

Besides, malodorous air is moved by the self-blowing function based on the centrifugal force produced by shearing forces between the air and the circular plates "a", "a", so that the turbulent-flow noise due to discharge of vortices downstream of blades (vanes), which is usually the case with sirocco fans and axial fans, is not generated in the present embodiment. Thus, the deodorizer fan F1 can be operated silently.

According to this embodiment, in particular, the circular plates "a" constituting the deodorizer fan F1 disposed on the rear side of the ozone generating block G1 are formed of a catalyst. Because the catalyst can thus be formed as integral part of the deodorizer fan F1, it is unnecessary to secure an extra space for placing the catalyst in the ozone deodorizing system M1. Consequently, it is possible to make the ozone deodorizing system M1 in a compact construction, thereby enabling easy incorporation of the ozone deodorizing system M1 into, for example, a toilet stool, a refrigerator or the like while minimizing the increase in the size of the toilet stool, refrigerator or the like due to the incorporation of the deodorizing system M1. This eliminates the need for coping with various problems arising from increases in size.

Figures 12, 12A:
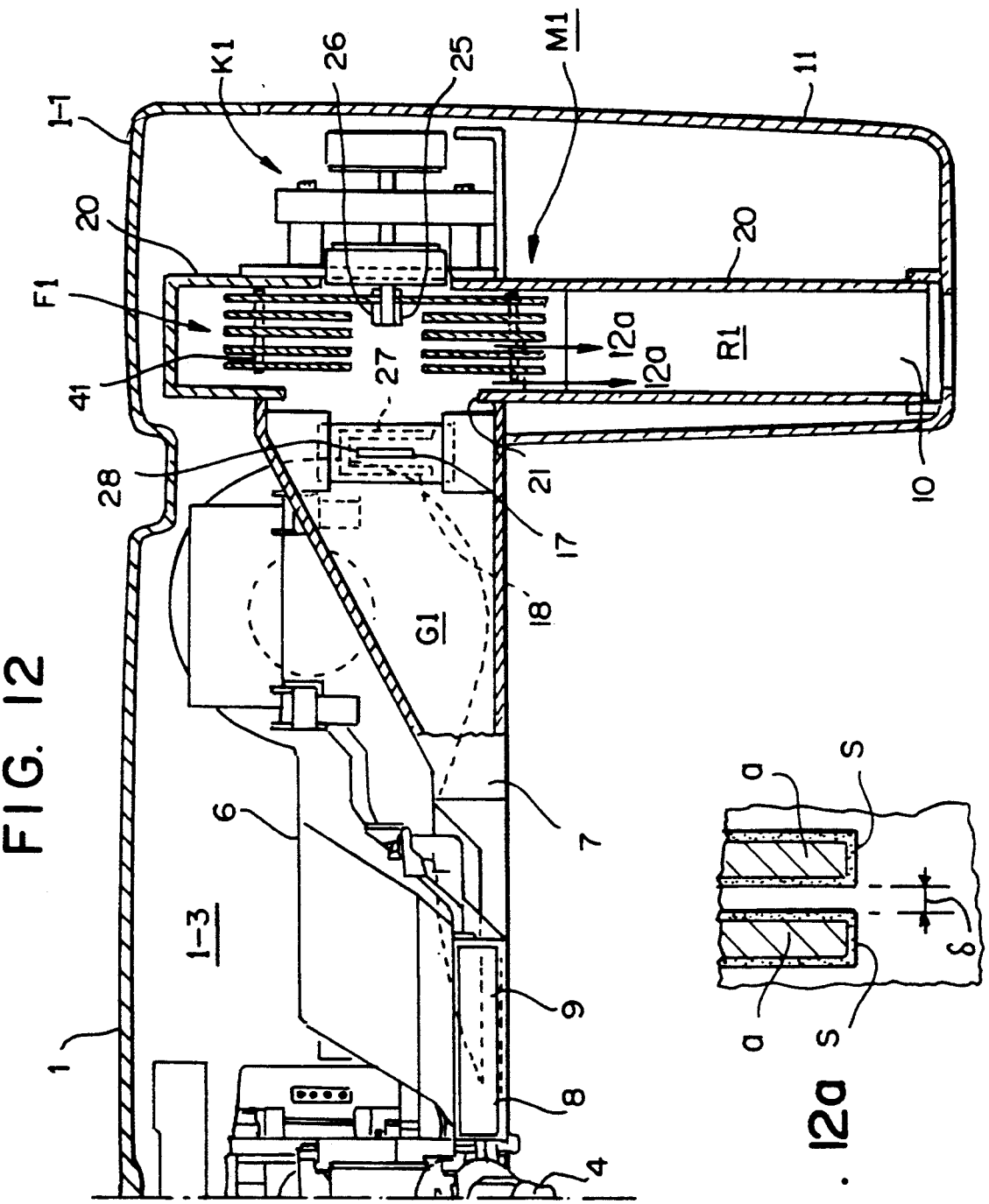
FIG. 12: A partly cutaway front view of an important part of an ozone deodorizing system according to another modification.
FIG. 12a: A sectional view of an area of FIG. 12 at lines 12a, 12a, showing plate spacing.

Referring now to FIGS. 12 and 12a, there is shown another embodiment. In this embodiment, a deodorizer fan F1 has a construction wherein a multi-layered stack of circular plates "a" formed of aluminum or a fibrous material is mounted on a boss portion 25, with a catalyst S supported on the surfaces of each circular plate "a".

In this case, just like the above case of using a catalyst for forming the circular plates "a", it is possible to increase the deodorizing treatment function and to operate the deodorizer fan F1 quietly.

In this embodiment, also, the catalyst S can be provided in one body with the deodorizer fan F1. Therefore, it is again unnecessary to secure an extra space for disposing the catalyst in the ozone deodorizing system M1, and to make the ozone deodorizing system A1 in a compact construction.

Figures 14, 14A:
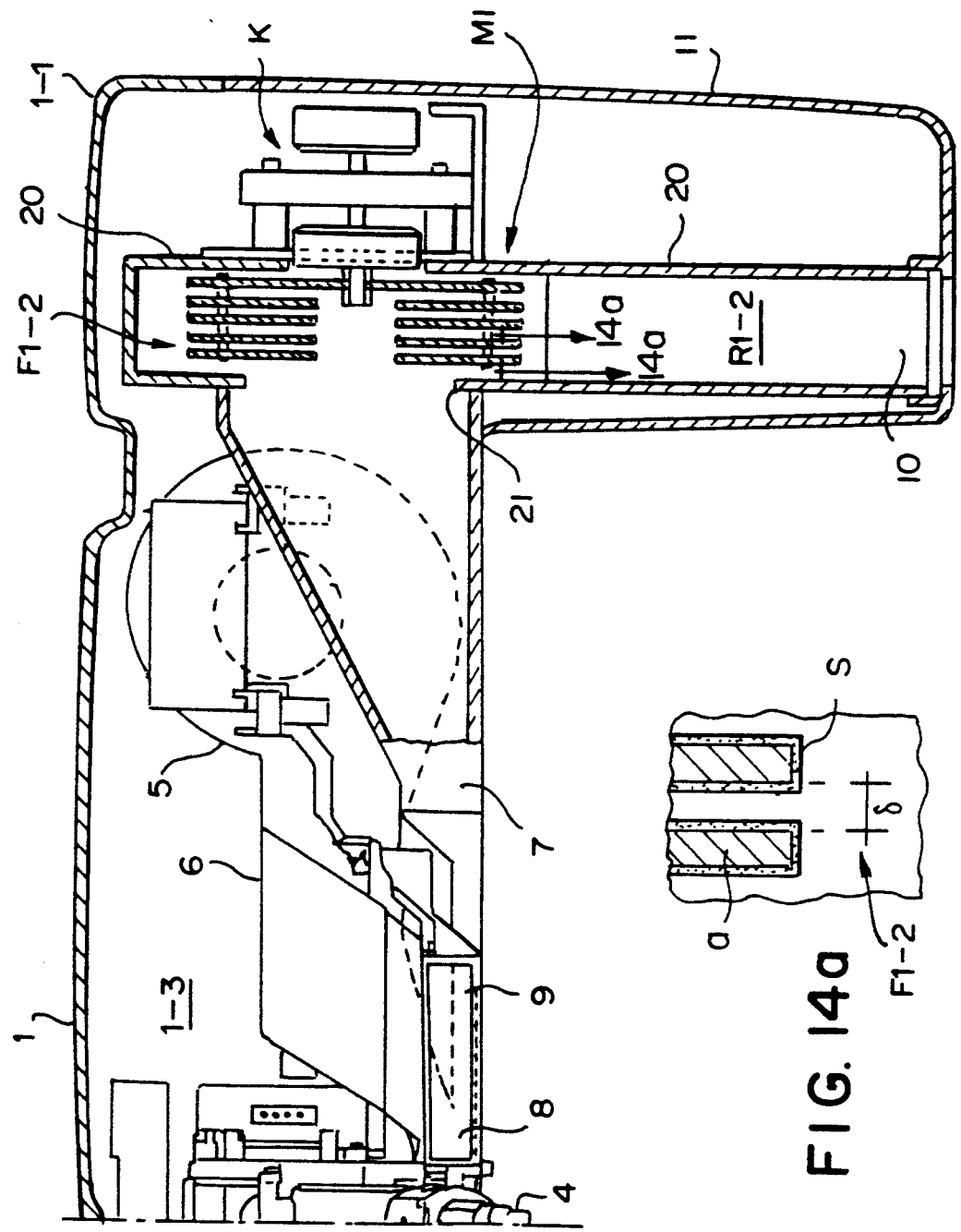
FIG. 14: A partly cutaway front view of an important part of an ozone deodorizing system according to yet another embodiment.
FIG. 14a: A sectional view of an area of FIG. 14 at lines 14a, 14a, showing catalyst coated plates and plate spacing.

FIGS. 13, 13a, 14, and 14a show further embodiments, in which a catalyst for decomposition of malodorous substances is used. As shown in FIGS. 13 through 14a, the general construction of the deodorizing systems of the present embodiments is the same as that of the deodorizing system described above with reference to FIGS. 7 to 10, except for the following point. While the above-described deodorizing system uses ozone for deodorization, the present deodorizing systems are designed for deodorization by use of the catalyst for decomposition of malodorous substances.

In the present embodiments, therefore, a deodorization duct 7 is not provided therein with an ozone generating portion G1. Instead, a deodorizer fan F1-1 comprising circular plates "a" formed of the malodorous-substance decomposition catalyst is disposed in a malodor treatment passage R1-1, as shown in FIG. 13, or a deodorizer fan F1-2 comprising the malodorous-substance decomposition catalyst S supported on the surfaces of circular plates "a" is disposed in a malodor treatment passage R1-2, as shown in FIG. 14.

As the catalyst for decomposition of malodorous substances, a variety of compositions may be used. Catalysts which can be used here include, for example, copper-ascorbic acid catalysts prepared by adding cuprous oxide and a binder (e.g. methyl cellulose) for decomposing a powder of a solid acid with high solid acid strength (e.g. aluminosilicate) and for fixing the cuprous oxide and solid acid, to an aqueous solution of L-ascorbic acid used as a preventive against oxidative deterioration of the cuprous oxide, thereby preparing a slurry, and impregnating therewith a synthetic paper made from rock wool (ceramic fibers).

Besides, where a catalyst for decomposition of ozone is applied to the circular plates, the resulting deodorizer fan can be applied, at low cost and with good performance, to decomposition of ozone, which is a harmful substance emitted from facsimile and copying machines.

Embodiment 3

Embodiment 3 will now be described below.

This embodiment relates to a modification of the above Embodiment 2, and is suitably applicable to decomposition of malodorous substances which have different constituents or different molecular structures.

Of the system used in this embodiments, the components or members which are the same as those in Embodiment 2 will be denoted by reference characters obtained by adding 100 to the corresponding reference characters used in Embodiment 2, respectively.

Figures 15, 15A:
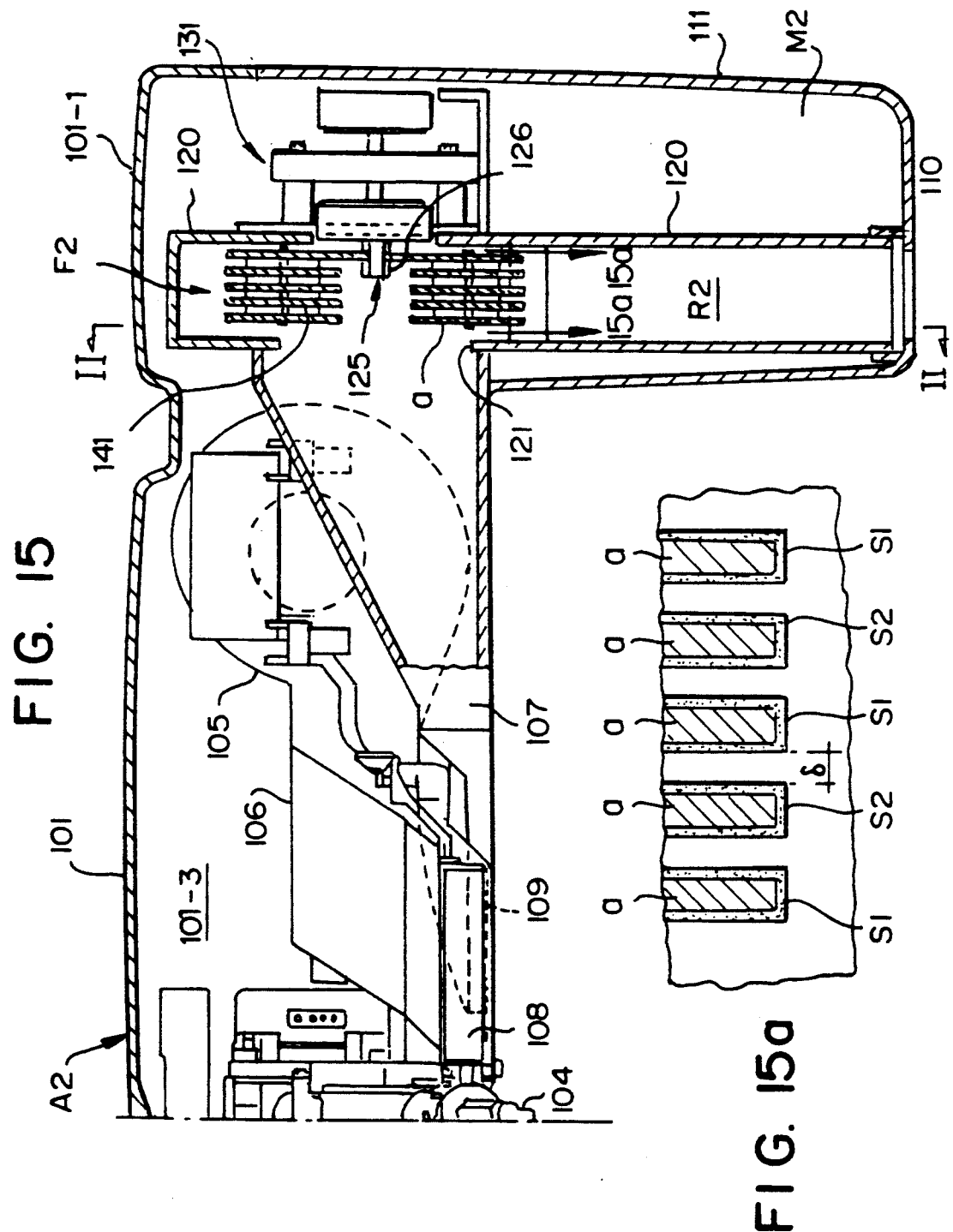
FIG. 15: A partly cutaway front view of an important part of a deodorizing system according to Embodiment 3.
FIG. 15a: A sectional view of an area of FIG. 15 at lines 15a, 15a, showing deodorant coated plates.
Figure 16:
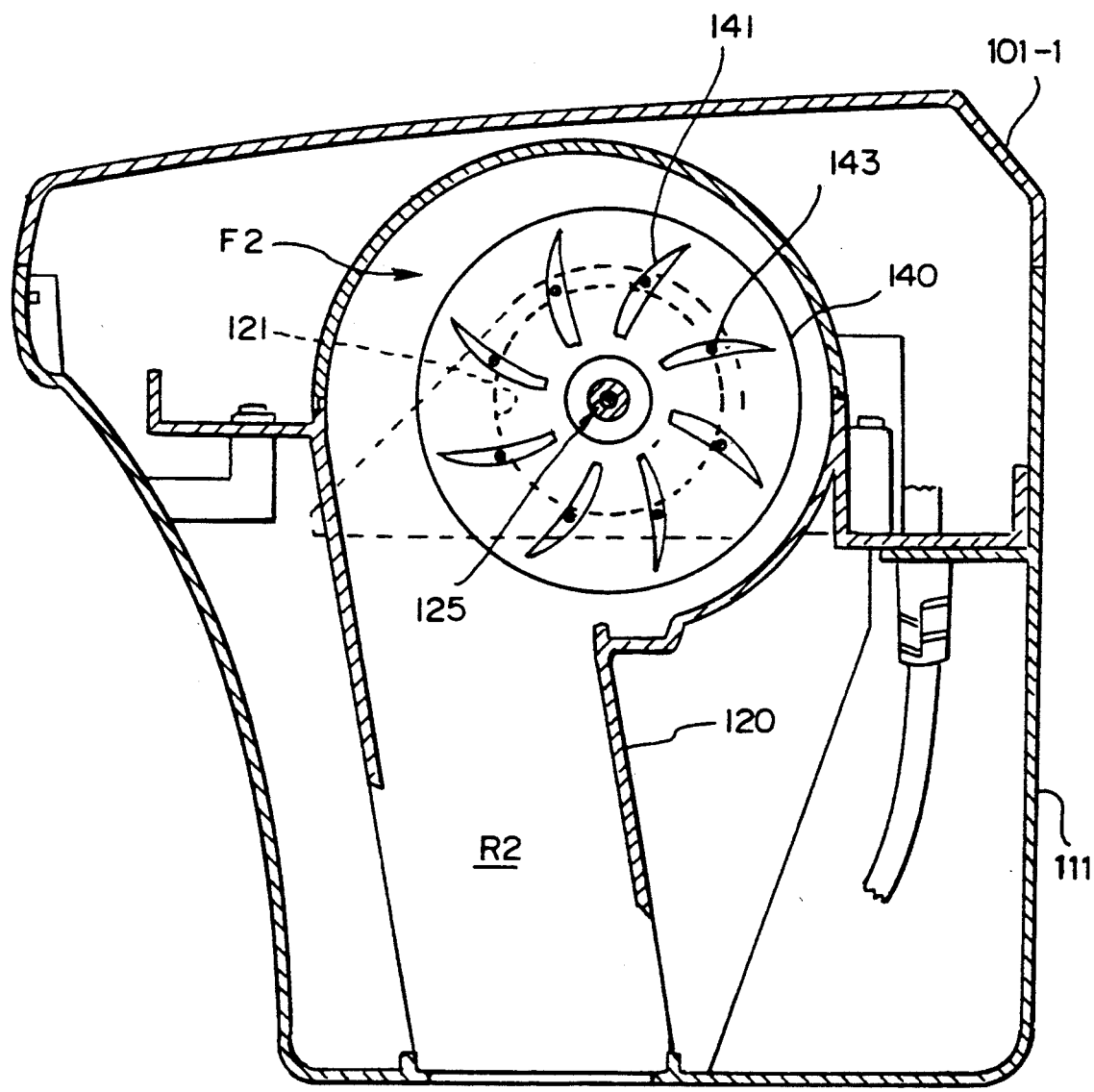
FIG. 16: A sectional side view of an important part of the deodorizing system taken along line II—II of FIG. 15.

As shown in FIGS. 15, 15a, and 16, a malodor treatment passage R2 communicates with the interior of a deodorization duct 107 through a communicating port 12 formed at an upper portion of the passage R2. In the upper portion of the malodor treatment passage R2, a deodorizer fan F2 substantially constituting an essential part of a deodorizing system M2 is rotatably mounted.

Fan blades of the deodorizer fan F2 in this embodiment are constructed by stacking annular circular plates "a" made of aluminum in a multi-layered configuration, with spacers 141 interposed so as to provide a predetermined spacing between adjacent ones of the circular plates "a", and mounting the stack on a boss portion 125. Deodorants $S_1$ and $S_2$ for respectively decomposing malodorous substances having different constituents or different molecular structures are supported on different ones of the circular plates "a" (on a plate basis) or on both surfaces or the same surface of each of the circular plates "a". Numeral 143 denotes securing pins for connecting the circular plates "a" firmly to each other.

Instead of supporting the deodorants $S_1$ and $S_2$ for decomposition of malodorous substances on different ones of the circular plates "a", the circular plates "a" themselves may be formed respectively from the deodorants $S_1$ and $S_2$ for decomposition of malodorous substances which have different constituents or different molecular structures.

Further, the circular plates "a" may be formed from a fibrous material and may each be impregnated with one or both of the deodorants $S_1$ and $S_2$, to thereby constitute the fan blades.

The deodorants $S_1$, for example, may be activated carbon, zeolite, aluminocilicate, while, the deodorants $S_2$ may be copper-ascorbic acid-oriented catalysts.

Thus, according to this embodiment, the deodorants $S_1$ and $S_2$ having different constituents or different molecular structures can be supported on different ones of the circular plates "a" or on both surfaces or the same surface of each of the circular plates "a". Even where the odor generated in the interior of a toilet stool body A2 is composed of a plurality of odorous components, therefore, a deodorizing effect can be securely attained by selecting the most suitable deodorants for decomposition of the respective odorous components.

The mounting of the multi-layered stack of the circular plates "a" on the boss portion 125, in the same manner as described in Embodiment 2 above, ensures that driving a motor 131 brings the circular plates a into rotation, thereby producing a self-blowing function. The self-blowing function enhances markedly the deodorizing treatment function, and it is therefore possible to provide a structurally simple and compact deodorizing system and to operate the deodorizer fan F2 silently.

Now, a deodorizing treatment process for removing malodors generated in the toilet stool body A2 by use of the deodorizing system M2 having the above construction will be explained, with reference to FIGS. 15 and 16.

First, with reference to FIG. 8, when the user is seated on a seat 2 of a toilet stool equipped with the ozone deodorizing system, a seating sensor T1 disposed on the rear side of the seat 2 sends a detection output to the control block D1, which produces a driving output to thereby drive the motor 131 of the deodorizer fan F2 of FIGS. 15 and 16.

As a result, the malodors generated in the interior of the stool body A2 are sucked into the malodor treatment passage R2, where the malodorous substances are decomposed into odorless components by the deodorants $S_1$ and $S_2$ supported on the circular plates "a" constituting the deodorizer fan F2. Thereafter, the exhaust air thus deodorized satisfactorily is discharged through an exhaust port 110 at the rear end of a hollow casing 120 into the toilet space.

Particularly, in this embodiment, the deodorants $S_1$ and $S_2$ can be provided as integral part of the deodorizer fan F2, so that there is no need to secure an extra space for placing the deodorants in the deodorizing system M2. It is therefore possible to make the deodorizing system M2 in a compact construction, thereby enabling easy incorporation of the system M2 into, for example, a toilet stool, a refrigerator or the like. Also, the compact construction makes it possible to minimize the increase in size of the toilet stool, refrigerator or the like due to the incorporation of the deodorizing system M2, and eliminates the need for coping with various problems arising from increases in size.

Besides, the deodorants $S_1$ and $S_2$ having different constituents or different molecular structures can be supported on different ones of the circular plates "a" (on a plate basis) or on both side surfaces or the same surface of each of the circular plates "a", as described above. Even where the odor generated in the interior of the toilet stool body A2 is composed of a plurality of odorous components, therefore, a deodorizing effect can be attained by selecting the most suitable deodorizers for decomposition of the respective odorous components.

Furthermore, the above descriptions made with reference to Embodiment 3 are also applicable to the cases where a combination of at least two catalysts, at least two adsorbents, at least two drying agents and at least two fragrant agents is used as an air-treating function imparted to the plate surfaces. It is therefore possible to perform a plurality of kinds of treatments with a single system.

Embodiment 4

Embodiment 4 will now be described below.

Figure 17:
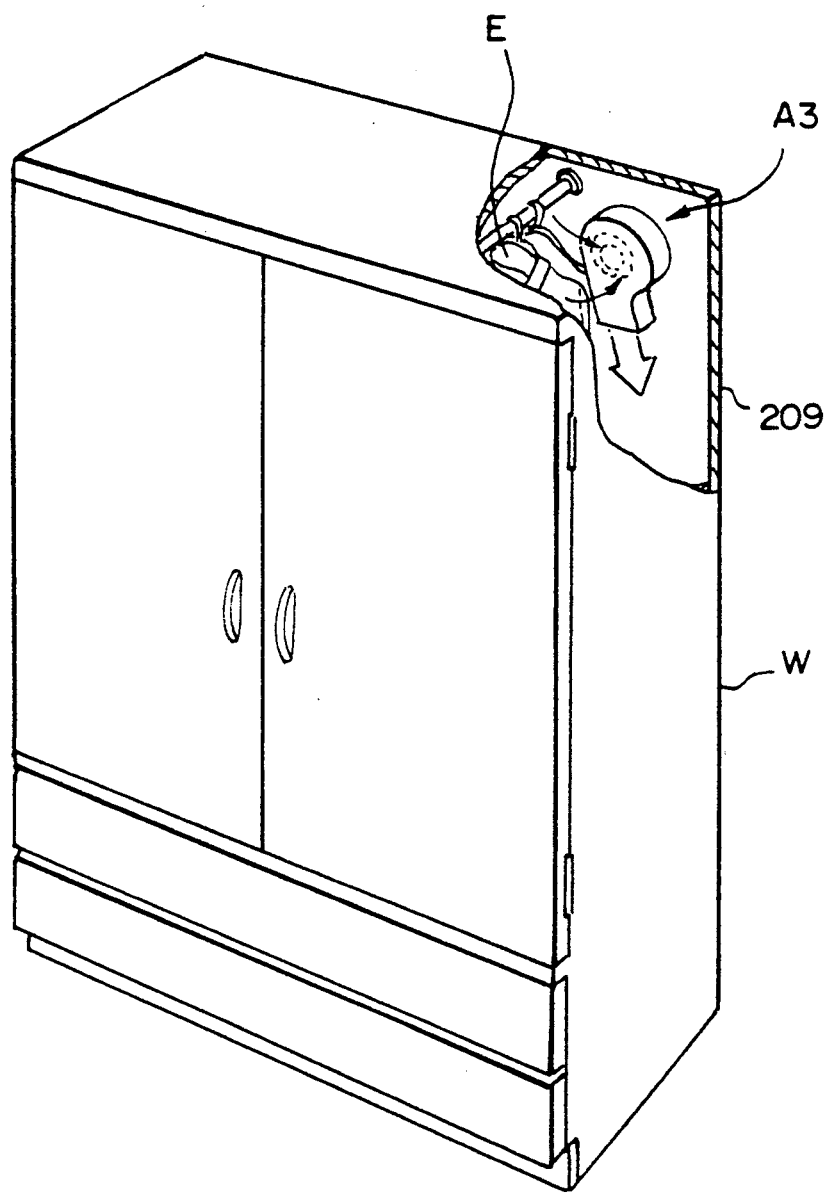
FIG. 17: A perspective view of a wardrobe fitted with a multi-stacked plate fan according to Embodiment 4.

Referring to FIG. 17, a drying fan A3 consisting of a multi-stacked plate fan is shown disposed in a wardrobe W in which clothes E are stored. In this embodiment, as shown in FIG. 18, the drying fan A3 is mounted on a back board 209 of the wardrobe W.

Figure 18:
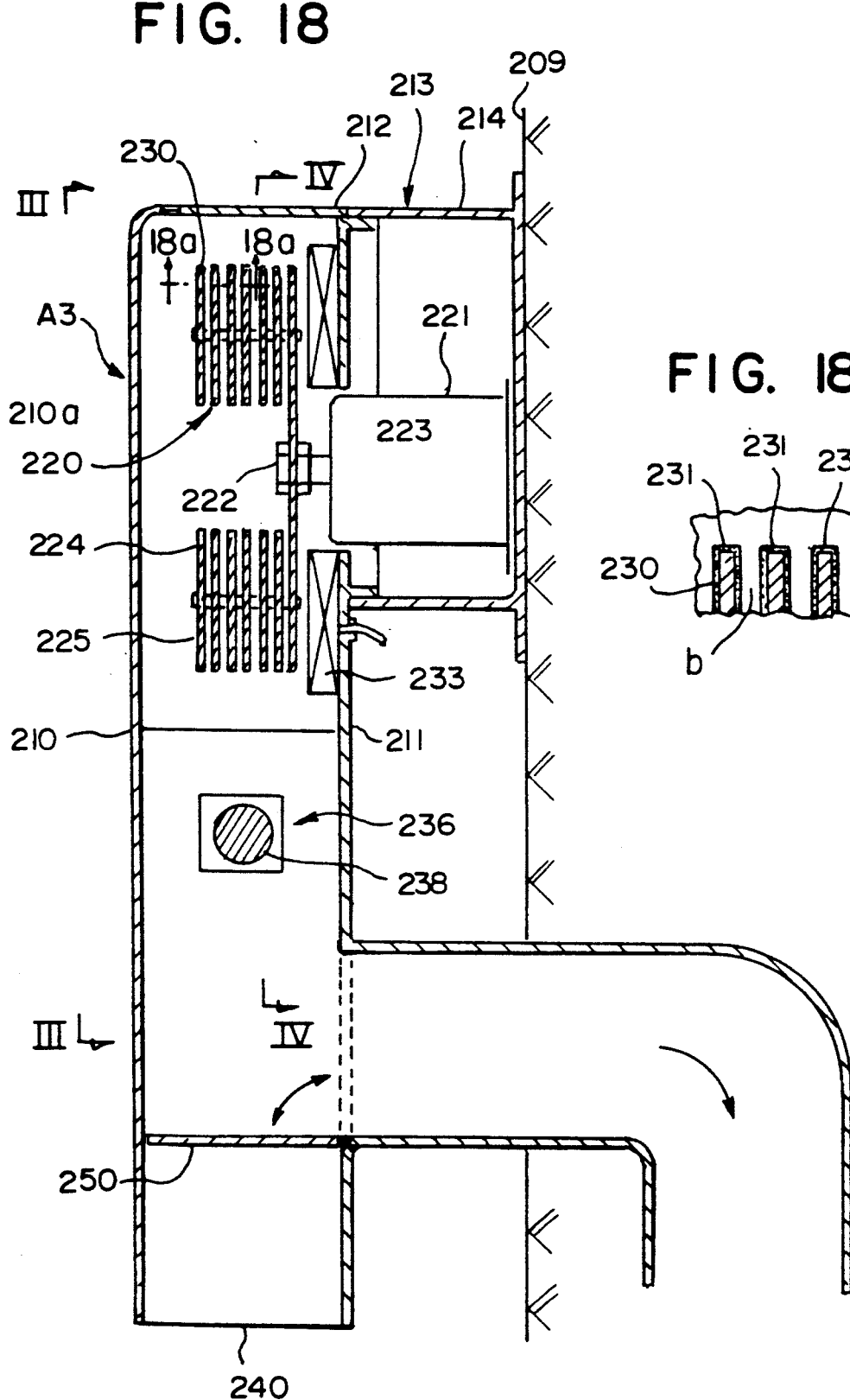
FIG. 18: A sectional front view of the multi-stacked plate fan.
Figure 18A:
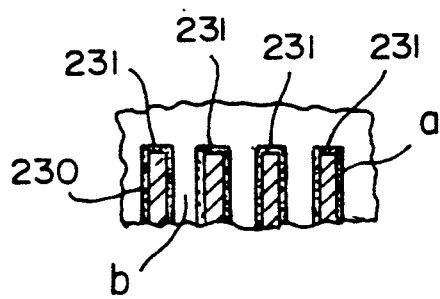
FIG. 18a: A sectional view of an area of FIG. 18 at lines 18a, 18a, showing a drying agent coating.
Figure 20:
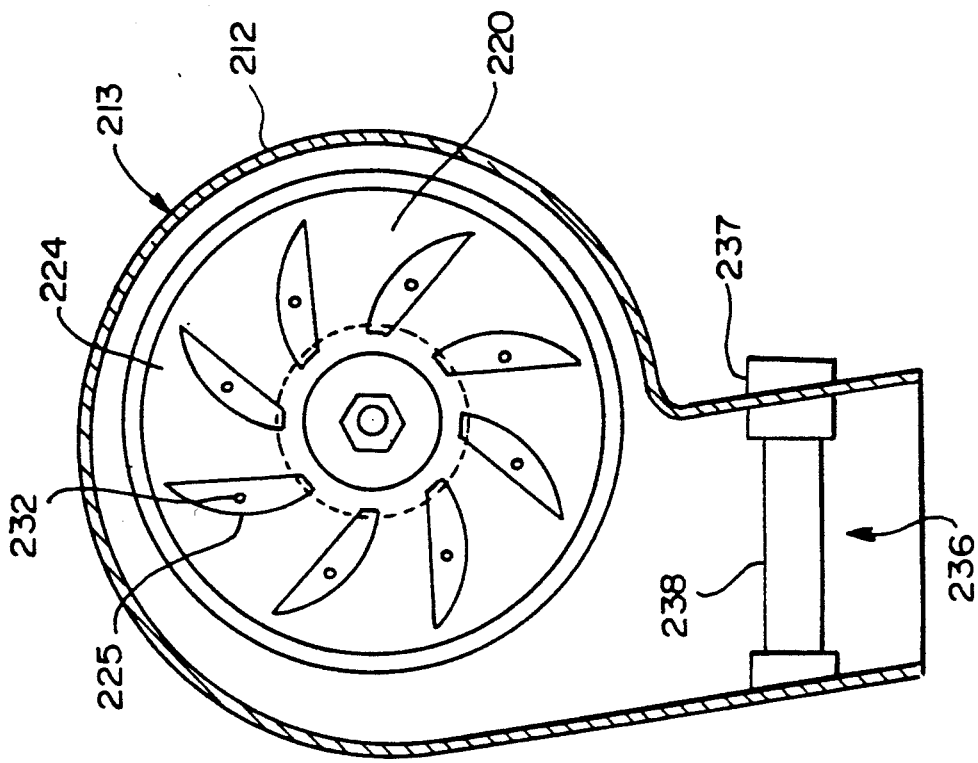
FIG. 20: A sectional view taken along line IV—IV of FIG. 18.
Figure 19:
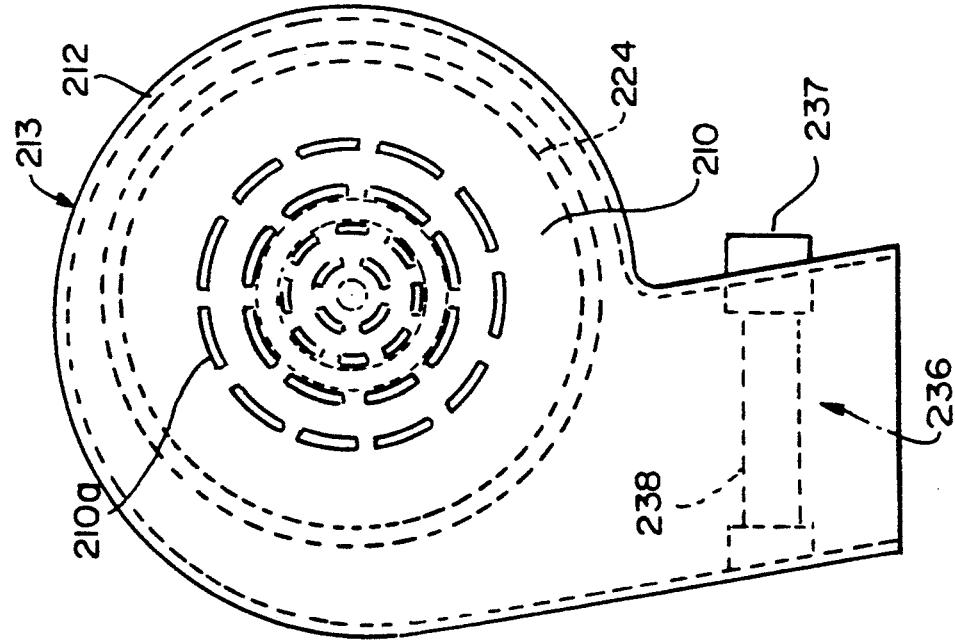
FIG. 19: A sectional view taken along line III—III of FIG. 18.

As shown in FIGS. 18 to 20, a fan casing 213 of the drying fan A3 comprises a front wall 210 and a rear wall 211 which are substantially circular and of which the circumferential edges, except a lower end opening portion (dry air outlet port) 240, are connected to each other by an annular peripheral wall 212.

The fan casing 213, in this embodiment, is attached to the back board 209 of the wardrobe W through a support frame 214.

The fan casing 213 is provided with an air intake port 210a formed in the front wall 210, and comprises fan blades 220 disposed concentrically therein. The fan blades 220 are connected to an output shaft 222 of a driving motor 221 disposed inside the support frame 214.

As shown in FIGS. 17 to 20, the fan blades 220 are constructed by stacking a multiplicity of annular circular plates "a" on a base circular plate 223, with spacers 225 interposed to provide a predetermined spacing between adjacent ones of the circular plates.

The annular circular plates "a" comprise annular circular plates 230 formed of aluminum which are stacked at regular intervals by interposing the spacers 225 so as to form a thin air layer b between adjacent ones of the circular plates 230, and a drying agent 231 such as silica gel is supported on both surfaces of each of the annular circular plates "a". Numeral 232 denotes securing pins for firm connection of the annular circular plates "a" to each other.

The drying agent 231 may be supported on only one surface, instead of on both surfaces, of each annular circular plate "a". Instead of supporting the drying agent 231 on each of the annular circular plates "a", besides, the annular circular plates "a" themselves may be formed from the drying agent 231.

Furthermore, the annular circular plates "a" may be formed from a fibrous material and impregnated with the drying agent 231, thereby forming the fan blades.

The drying agent 231 is not limited to the above-mentioned silica gel but may be zeolite, calcium chloride, active alumina or the like.

Thus, according to this embodiment, the fan blades 220 of the drying fan A3 are constructed by supporting the drying agent 231 on the annular circular plates "a" stacked in a multi-layered configuration, and air is moved by centrifugal forces generated by shearing forces acting between the air and each of the annular circular plates "a", "a". It is therefore possible to secure a sufficient area of contact between humid air and the drying agent 231, leading to a further increase in drying efficiency. In addition, the generation of turbulent-flow noise due to discharge of vortices on the downstream of blades, usually experienced with sirocco fans and axial fans, is obviated and a very quiet operation of the drying fan A3 is accordingly ensured.

In this embodiment, further, an annular ceramic heater 233 capable of heating by passing an electric current is disposed between the rear wall 211 of the fan casing 213 and the base circular plate 223 for the fan blades 220. When drying is unnecessary or in other similar situations, the heater 233 is operated to heat the fan blades 220 wholly so as to discharge the moisture trapped by the drying agent, whereby the capability of the drying agent can be restored and a longer-lived drying effect can be obtained. In this case, a passage to the exterior of the wardrobe W is additionally provided so as to discharge the moisture through a selector damper 250 when the heater 233 is operated.

In FIG. 20, reference character 236 denotes a UV germicidal system disposed at the rear of the fan blades 220, the system comprising a germicidal power supply 237 and a UV lamp 238.

Now, the drying operation for the interior of the wardrobe W by the drying fan A3 with the above construction will be explained, with reference to FIGS. 18 and 20.

First, when an operating switch (not shown) is depressed by the user, the fan driving motor 221 is operated.

By the drive of the motor 221, the fan blades 220 are rotated to draw humid air from the outside into the fan casing 213. The humid air thus introduced is caused to pass between the circular plates "a", "a" constituting the fan blades 220, before forming a downward air flow to be blown out of the fan casing 213 through the dry air outlet port, i.e. lower end opening portion 240.

The dried air thus blown out of the fan casing 213 is circulated in the wardrobe W, is then taken again into the fan casing 213 of the multi-stacked plate fan A3, to be dried in the manner as above, and is again discharged into the wardrobe W.

Thus, according to this embodiment, it is possible by operating the drying fan A3 to constantly circulate dry air in the wardrobe W, and to thereby minimize the development or growth of fungi on the clothes E and the like. Particularly where the fan blades 220 are composed of a multiplicity of annular circular plates "a" with a multi-stacked construction, passage of air between the annular circular plates "a", a provides a broad area for absorption of moisture and enables a uniform and rapid drying, thereby leading to an enhanced drying efficiency.

In addition, by operating the ceramic heater 233 and switching over the selector damper 250 when drying is unnecessary or in other similar situations, it is possible to discharge the moisture trapped by the drying agent, and to thereby maintain the drying effect of the drying agent.

Furthermore, not only drying but also sterilization can be achieved, by the UV germicidal system 236.

Embodiment 5

Embodiment 5 will now be described below.

Figure 21:
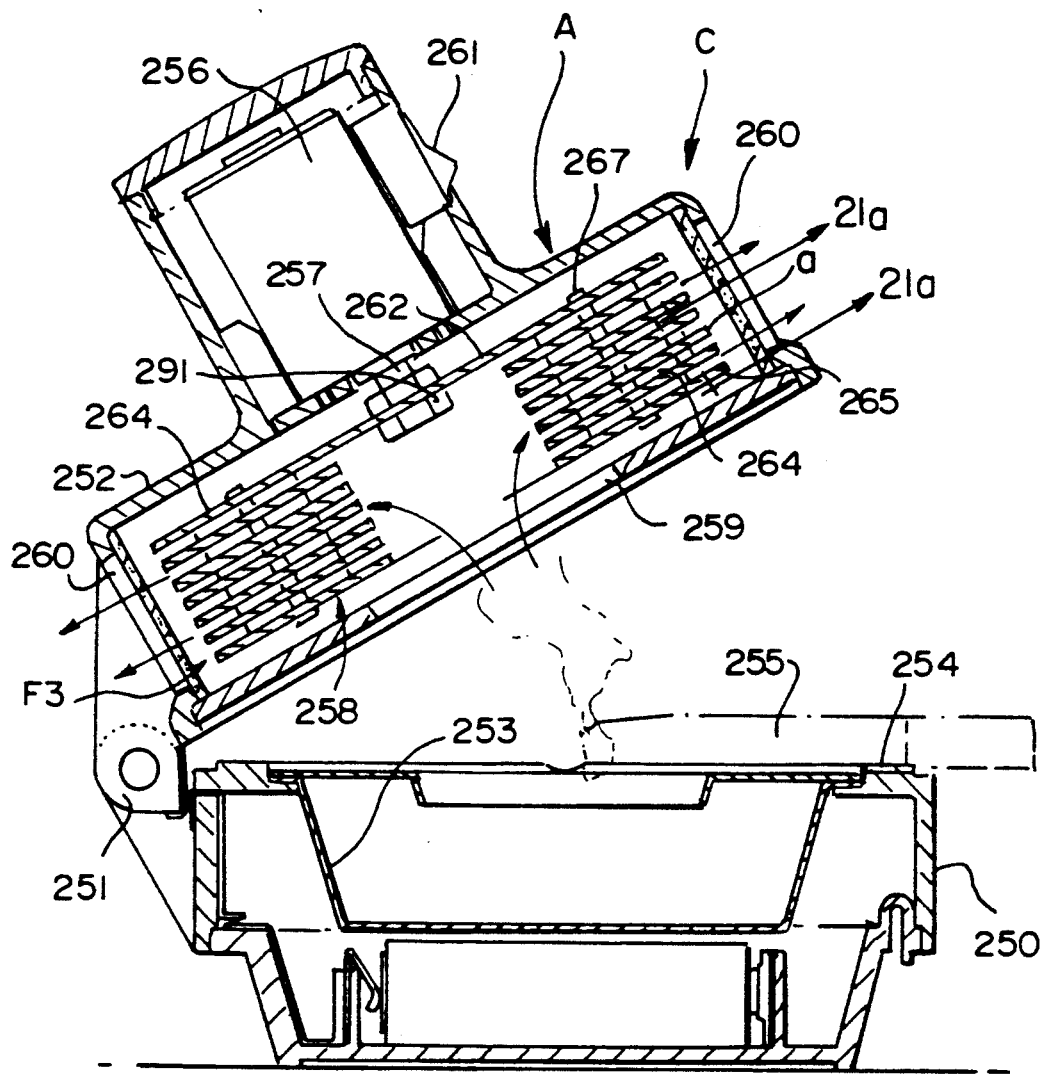
FIG. 21: A sectional view of a dust collector fitted with a multi-stacked plate fan according to Embodiment 5.
Figure 22:
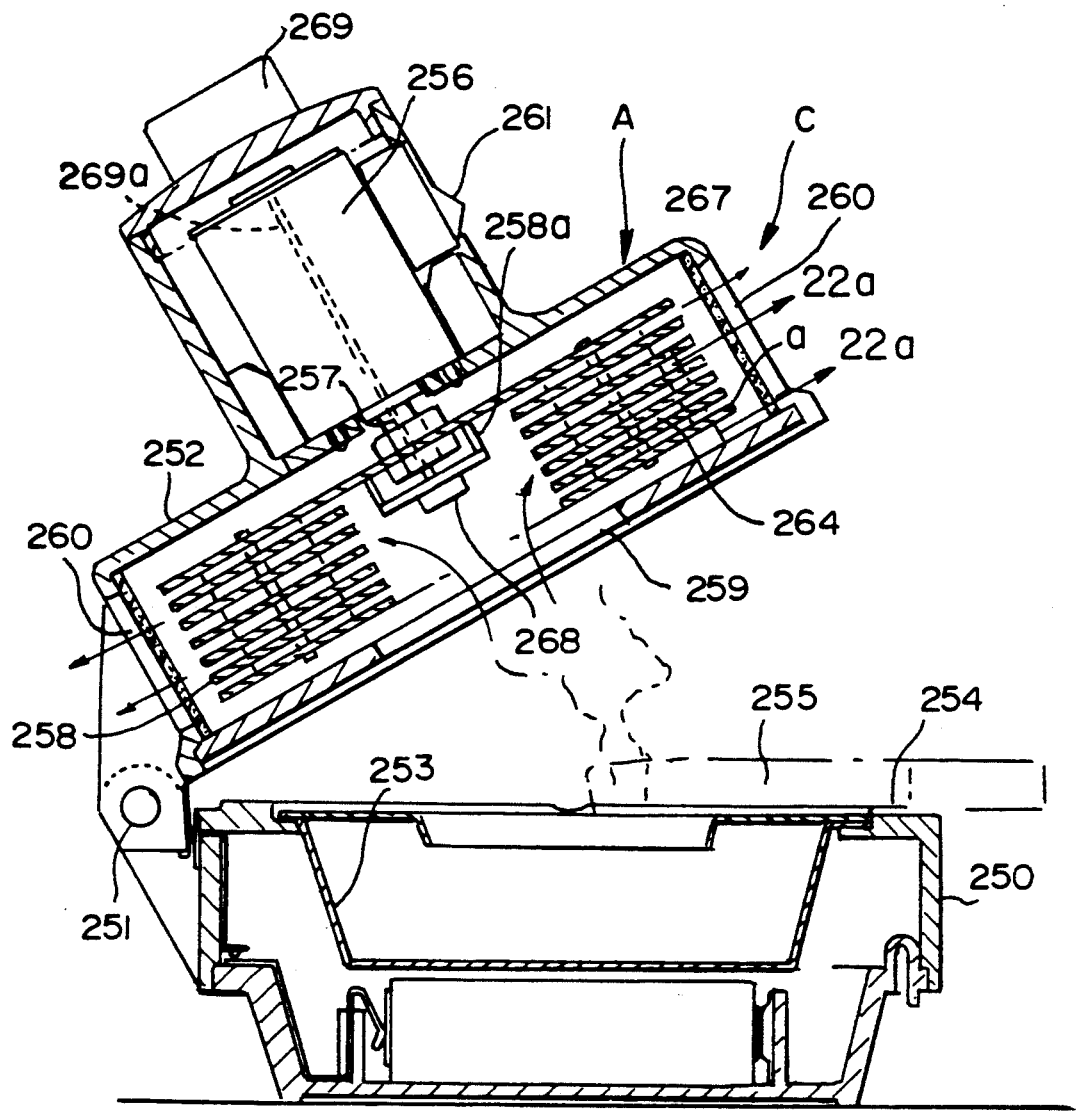
FIG. 22: A sectional view of a dust collector according to a modification.

This embodiment, as shown in FIGS. 21 and 22, relates to a system in which a air-treating function is collection, or removal, of smoke emitted from tobacco or the like.

Figure 21A:
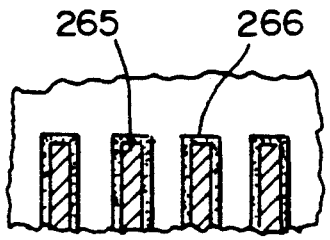
FIG. 21a: A sectional view of an area of FIG. 21 at lines 21a, 21a, showing deodorant coated plates.

Referring to FIGS. 21 and 21a, there is shown a smoke/dust collector C of which the air-treating function is collection (removal) of smoke emitted from a cigarette or the like. The smoke/dust collector C comprises a circular, hollow lower casing 250 and a circular, hollow upper casing 252 openably connected to one end portion of the lower casing 250 through a pivotal joint portion 251. An ashtray 253 for collecting tobacco ash is contained in the lower casing 250, and a cigar or cigarette 255 is put on a cigar/cigarette rest portion 254 to permit tobacco ashes to fall into the ashtray 253.

In an upper portion of the upper casing 252 is disposed a motor 256 with an output shaft 257 projected downward, and fan blades 258 are rotatably connected to the output shaft 257 of the motor 256. The upper casing 252 is provided in a lower surface thereof with a smoke intake port 259 for sucking in the smoke, and is provided in a peripheral surface thereof with a plurality of smoke exhaust ports 260 through which the smoke drawn in by the fan blades 258 is exhausted in the direction of the circumference. Denoted by 261 is a switch for the motor 256.

The fan blades 258, as shown in FIG. 21, comprise a multiplicity of annular circular plates "a" stacked on a base circular plate 262 in a multi-layered configuration, with spacers 264 interposed so as to form a predetermined spacing between adjacent ones of the circular plates.

The annular circular plates "a" are constructed by mounting a multi-layered stack of annular circular plates 265 formed of aluminum, which are spaced in a predetermined manner by the spacers 264, on the base circular plate 262. A deodorant 266 such as active carbon, zeolite, aluminosilicate, etc. is supported on both side surfaces of each of the annular circular plates "a" as shown in FIG. 21a. Numeral 267 denotes securing pins for firm connection of the annular circular plates "a", to each other.

The deodorant 266 may be supported on only one surface, instead of on both surfaces, of each annular circular plate "a". Instead of supporting the deodorant 266 on each of the annular circular plates "a", each annular circular plate 265 may be made of the deodorant 266 per se and further, the annular circular plates "a" themselves may be formed from a fibrous material and the annular circular plates 265 may be impregnated with the deodorant 266, thereby forming the fan blades.

The deodorant 266 is not limited to the examples mentioned above; for instance, the copper-ascorbic acid catalyst described in Embodiment 2 above and the like can also be used as the deodorant.

Because the circular plates "a" are mounted on the boss portion 291 in the form of a multi-layered stack, in the same manner as described in Embodiment 2 above, driving the motor 256 causes the circular plates "a" to rotate, thereby producing a self-blowing function. The self-blowing function enhances the deodorizing treatment function markedly, and it is therefore possible to provide a structurally simple and compact deodorizing system and to ensure a silent operation of the smoke/dust collector C.

Figure 22A:
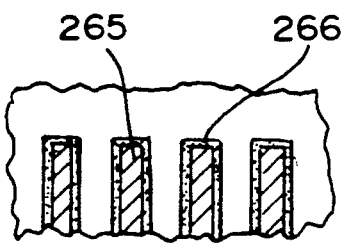
FIG. 22a: A sectional view of an area of FIG. 22 at lines 22a, 22a, showing deodorant coated plates.

In addition, as shown in FIGS. 22 and 22a, an ozonizer 268 as an ozone generator is mounted on a support base 258a situated centrally to the fan blades 258, and a high voltage generator 269 operated by a switch 261 is disposed at an upper portion of the upper casing 252. The ozonizer 268 is connected with a cord 269a, which is led from the high voltage generator 269 by passing through the output shaft 257 of the motor 256.

With the construction as above, rotation of the fan blades 258 causes the tobacco smoke taken in and ozone fed from the ozonizer 268 to mix with each other, resulting in deodorization by ozone. Further, a smoke-decomposing treatment is performed by the deodorant 266 at the fan blades 258, and the thus treated smoke is exhausted via the smoke exhaust port 260. Thus, an effective deodorizing is achieved.

The treatment process by use of the smoke/dust collector C with the above construction will now be explained in detail below, with reference to FIGS. 21 and 22.

First, the upper casing 252 of the smoke/dust collector C is opened to an inclined position. Then the switch 261 is operated to drive the motor 256, thereby rotating the fan blades 258, and the high voltage generator 269 is driven.

As a result, the smoke emitted from the cigar or cigarette 255 rested on the lower casing 250 is sucked in through the smoke intake port 259 in the upper casing 252, and the smoke thus introduced is decomposed by or adsorbed on the deodorant 266 at the fan blades 258. In addition, the smoke is mixed with the ozone supplied from the ozonizer 268 provided inside the fan blades 258, whereby an effective deodorizing treatment is performed.

Thereafter, the smoke thus deodorized is exhausted into the atmosphere through the smoke exhaust ports 260 formed in the circumferential surface of the upper casing 252.

Embodiment 6

Figure 23:
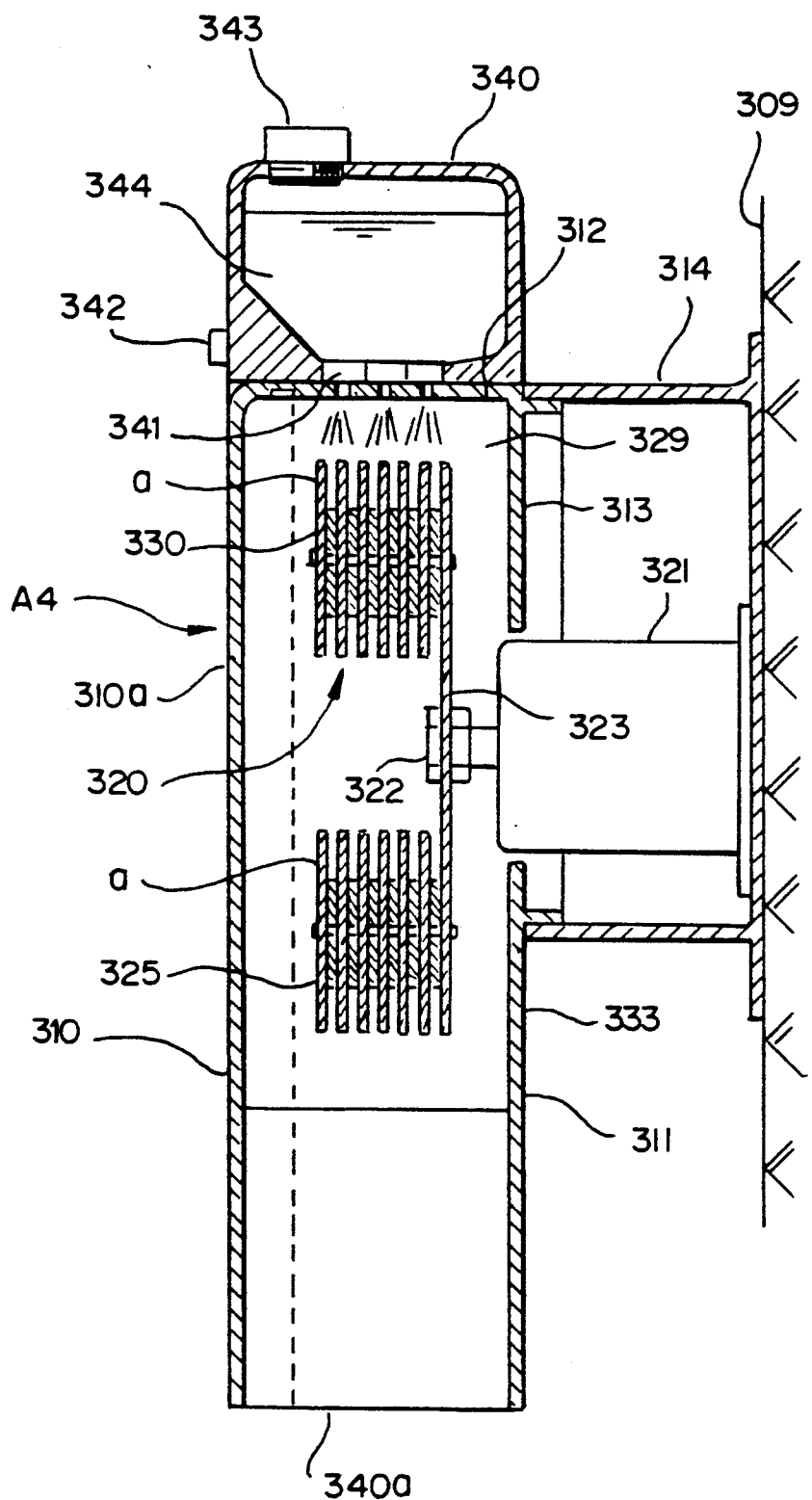
FIG. 23: A sectional view of a fragrance-releasing system according to Embodiment 6.

Embodiment 6 will now be explained below, with reference to FIG. 23.

The basic construction of the system used in the embodiment is the same as that of the drying fan of Embodiment 4; therefore, explanations of the basic construction will be omitted, and only characteristic parts of the system will be explained in detail.

This embodiment relates to a fragrance fan, which is attached to a wall portion of a living room, a toilet or the like through a support frame 314.

Annular circular plates "a" are each formed in an annular form from a porous material, which can be easily impregnated with a liquid, for example, a fragrant liquid.

At an upper portion of an annular peripheral will 312, a tank 340 is provided for reserving a fragrant liquid 344. A means 341 for spraying the fragrant liquid 344 toward the annular circular plates "a" is disposed between the tank 340 and an interior space 329 of a fan casing.

The spray means 341 is operated electrically, by depressing a spray operating button 342 provided at a front face portion of the tank 340, to spray the fragrant liquid 344 toward the annular circular plates "a" for a predetermined period.

A screw-type cap 343 is provided at an upper portion of the tank 340 so that when the fragrant liquid 344 contained in the tank 340 runs out, the tank 340 can be replenished with the fragrant liquid 344 via a fragrant liquid supply hole by removing the cap 343.

The fragrant liquid 344 may be any one of those liquid fragrant agents which are in common use, such as glyoxal, methacrylic acid esters, perfumes, etc.

Now, the fragrance-releasing operation of the fragrance fan A4 with the above construction will be explained.

First, when the spray operating button 342 is depressed by the user before operation of the fragrance fan A4, the fragrant liquid 344 is sprayed toward the annular circular plates 330 in the interior spacing 329 of the fan casing, so that the porous annular circular plates 330 are impregnated with the fragrant liquid 344.

Then, an operating button (not shown) for the fragrance fan A4 is depressed to operate a fan driving motor 321. By the drive of the motor 321, the fan blades 320 are rotated to draw air from the exterior into the fan casing 310. The air thus drawn in is passed between the annular circular plates "a", a constituting the fan blades 320, and is then discharged to the exterior through an air outlet port 340a.

Because the air is passed between the annular circular plates "a", a impregnated with the fragrant liquid 344, the air can be blown out through the air outlet port 340a after being given a sufficient fragrance by an action similar to those in the above embodiments.

For forming the annular circular plates "a", fibrous or other materials may also be used, instead of porous material, provided that the materials are capable of being impregnated with liquids.

At the time of spraying the fragrant liquid 344, the annular circular plates "a" may be rotated slowly, in order to ensure uniform infiltration of the fragrant liquid 344 throughout the annular circular plates "a". Besides, the spraying of the fragrant liquid 344 may not necessarily be carried out prior to the operation of the fragrance fan A4, but may be carried out periodically, e.g. once a day, and automatically, e.g. by use of a timer.

Furthermore, this embodiment naturally is applicable to deodorizing or other operations by use of a deodorizing liquid or the like, as well as to the fragrance-releasing operation.

Embodiment 7

This embodiment relates to the basic construction of an air treatment system having a high air-treating capacity and capable of silent operation, comprising a multi-stacked plate fan constructed by stacking a multiplicity of annular circular plates with regular spacings therebetween, wherein a multiplicity of vanes are interposed between the annular circular plates, and the outer ends of the vanes are located at a predetermined distance to the inner side from the outer circumferential edge of the annular circular plate; One specific example is illustrated in FIGS. 24 to 28.

Figure 24:
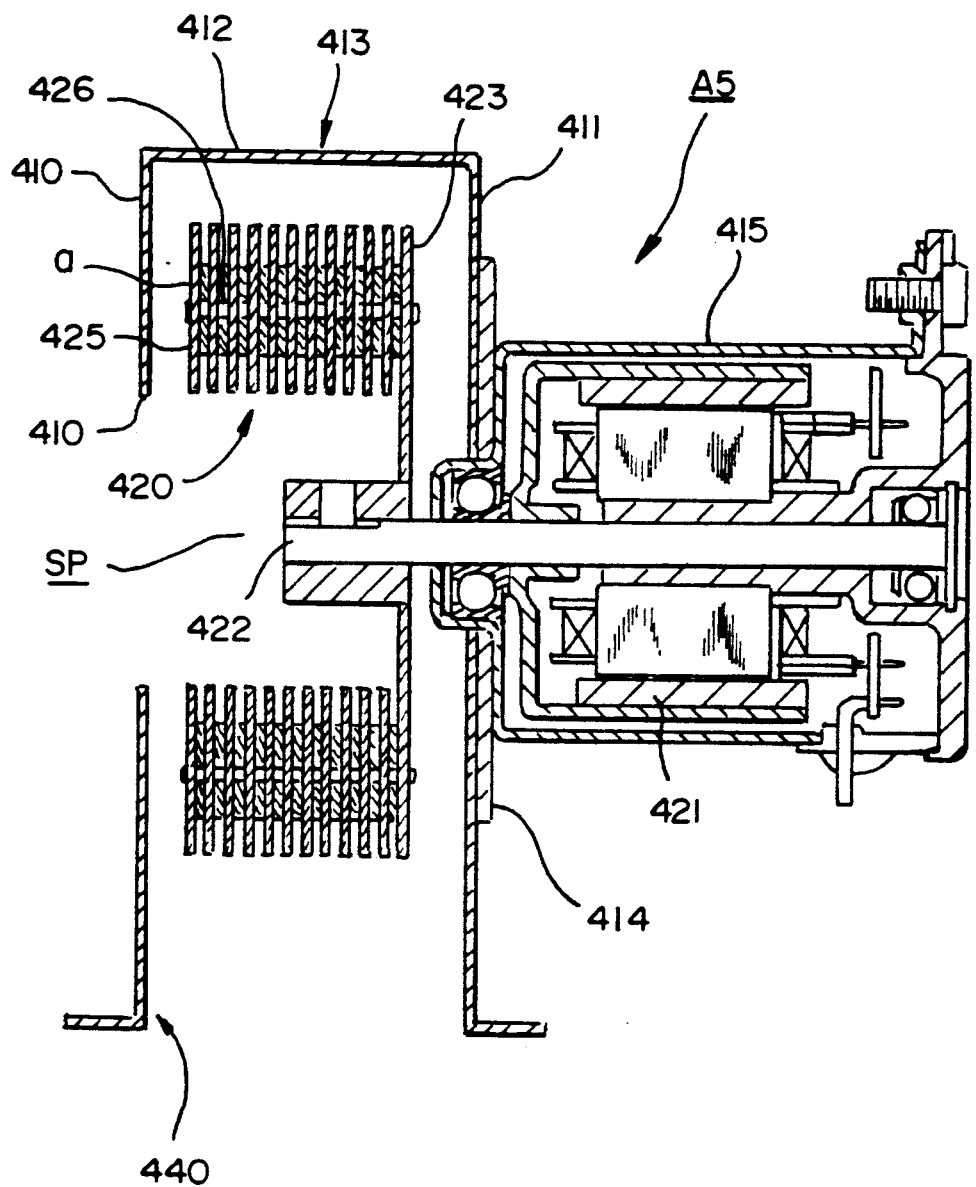
FIG. 24: A sectional view of an air treatment system according to Embodiment 7.
Figure 25:
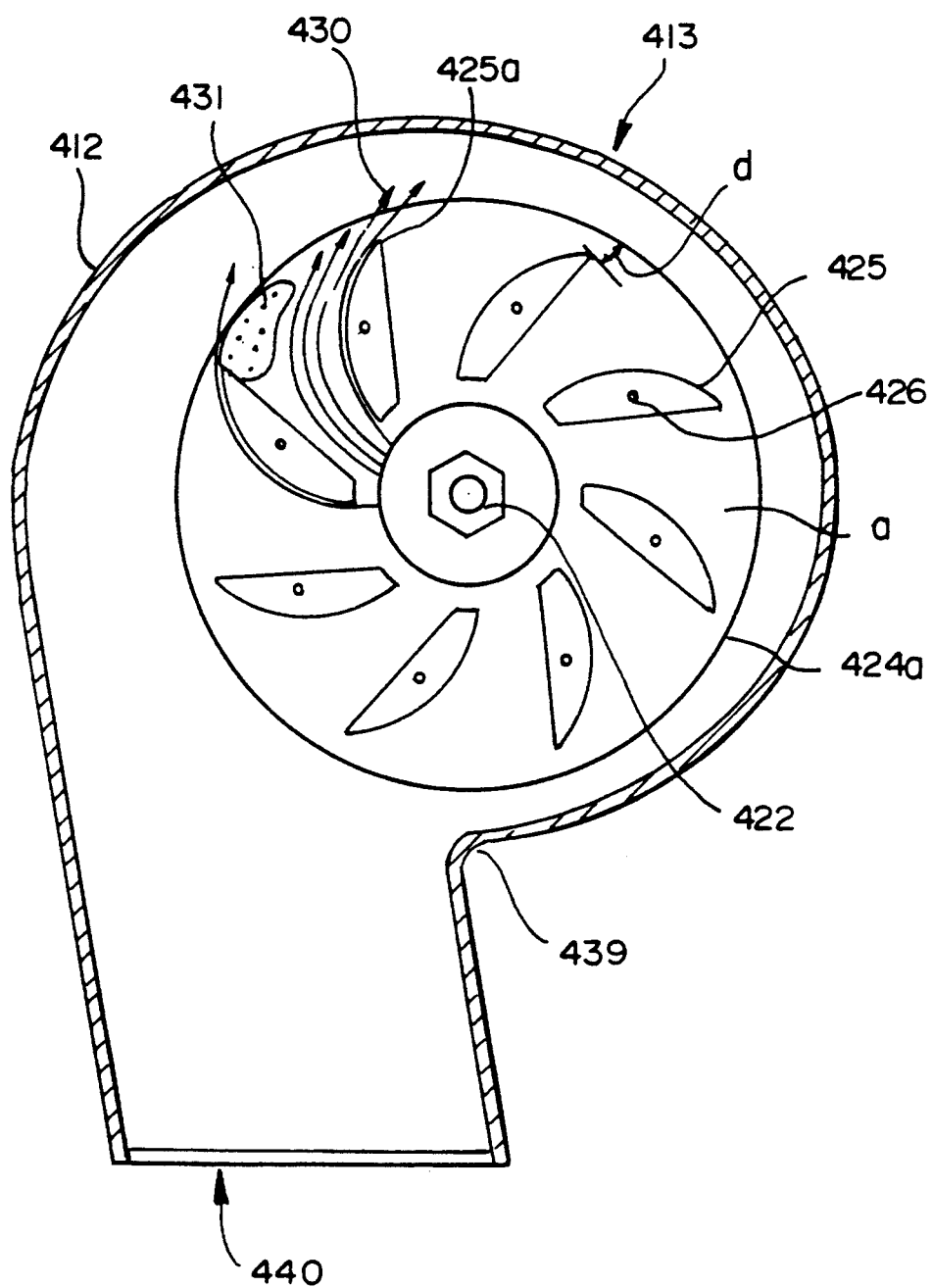
FIG. 25: A front sectional view of the air treatment system of FIG. 24.

As shown in FIGS. 24 and 25, a fan casing 413 of the multi-stacked plate fan A5 comprises a front wall 410 and a rear wall 411 which are substantially circular and of which the circumferential edges, except a lower end opening portion 440, are joined to each other by an annular peripheral wall 412.

The fan casing 413, in this embodiment, is attached to a motor casing 415 through a support frame 414.

The fan casing 413 is provided in the front wall 410 thereof with an air intake port 410a, and comprises fan blades 420 disposed concentrically therein. The fan blades 420 are connected to an output shaft 422 of a fan driving motor 421 disposed in the support frame 414.

In the basic construction as above, a characteristic feature of this embodiment lies in the construction of the fan blades 420 having a high air-treating capacity and capable of silent operation.

Figure 26:
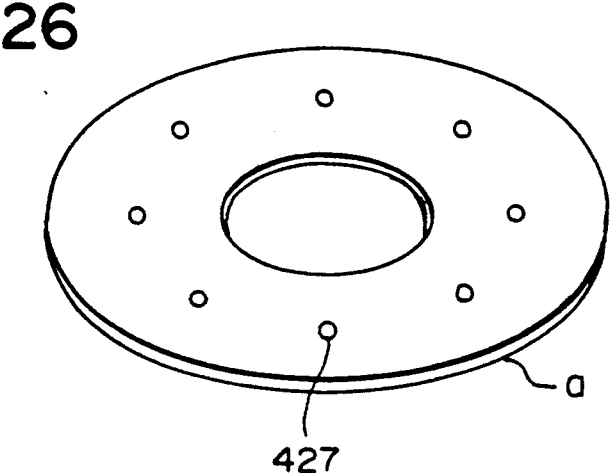
FIG. 26: A perspective view of an annular circular plate used in the air treatment system of FIG. 24.
Figure 27:
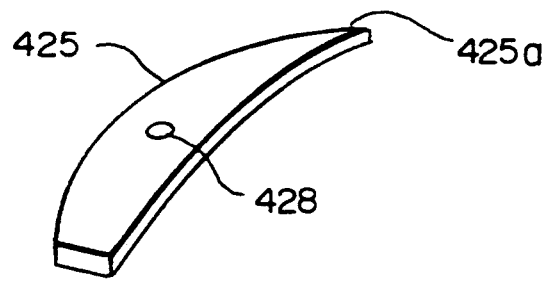
FIG. 27: A perspective view of a vane used in the air treatment system of FIG. 24.

That is, as shown in FIGS. 24, 26 and 27, the fan blades 420 are constructed substantially by stacking a multiplicity of the thin annular circular plates "a" having surfaces treated with a deodorant as has been described in Embodiment 2, on a base circular plate 423 in a multi-layered configuration with a multiplicity of the vanes 425 interposed so as to provide a predetermined spacing between adjacent ones of the circular plates.

The annular circular plates "a" are each formed in annular shape, as shown in FIG. 26, and are provided with insertion holes 427 at a desired angular pitch, for insertion therethrough of connecting pins 426, which will be described below.

On the other hand, each of the vanes 425 is constituted of a thin arcuate piece, as shown in FIG. 27, and is provided at a central portion thereof with an insertion hole 428 for passing the connecting pin 426 therethrough.

To assemble the fan blades 420 as shown in FIG. 24, the multiplicities of annular circular plates "a" and vanes 425 are stacked alternately with each other on the base circular plate 423 by passing the connecting pins 426 through the respective insertion holes 427 and 428. Then, the leading ends of the connecting pins 426 thus inserted are caulked onto the surface of the last annular circular plate "a", thereby completing the assembly of the fan blades 420.

With the multiplicity of vanes 425 thus disposed in each spacing between adjacent ones of the annular circular plates "a", "a", rotation of the fan blades 420 results in an air-blowing function generated due to the rotation of the annular circular plates "a" and augmented by the action of the vanes 425. Therefore, an increased air-treating capacity can be achieved.

Further, in this embodiment, as is most clearly seen from FIG. 25, all of the vanes 425 have their outer end portions 425a located at a predetermined distance d to the inner side from the outer circumferential edge of the annular circular plate "a".

When the fan blades 420 are rotated, therefore, air is caused to flow from a central space SP formed inside the multi-stacked annular circular plates "a", and then radially through the thin air layers b between the annular circular plates "a", a toward the outside of the fan blades 420, to be discharged from the annular circular plates "a" to the exterior. In this case, the turbulence due to separation of flow at the rear of the vanes 425 or the disturbance 431 due to waves discharged from the vanes 425, which might be generated between the annular circular plates "a", a, can be inhibited by viscosity arising from wall surfaces. Therefore, the generation of turbulent-flow noise due to such turbulence or disturbance can be prevented effectively.

Figure 28:
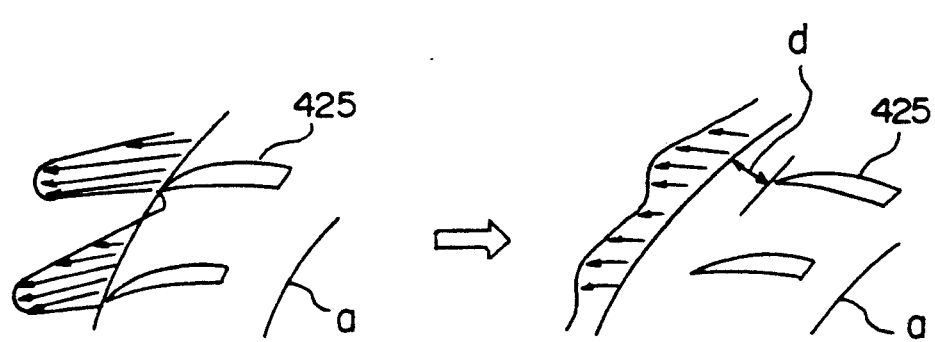
FIG. 28: An illustration of how the generation of turbulent flow is inhibited by the air treatment system of FIG. 24.

Moreover, the arrangement of the outer edge portions 425a at the predetermined distance d to the inner side from the outer circumference of the annular circular plate a produces the following effects. When air is discharged from the annular circular plates "a" of the multi-stacked plate fan A5, the distribution of discharge velocities of the treated air at exit from the annular circular plates "a" has an improved uniformity, as shown in FIG. 28. Therefore, there is no noise due to interference of air with a tongue portion 439 of the fan casing 413. Because of little distortion of the discharge velocity of air, in addition, it is possible to effectively prevent the generation of turbulent-flow noise arising from distorted air velocity.

Now, the operation of the multi-stacked plate fan A5 with the above construction will be described, with reference to FIGS. 24 and 25.

First, when an operating switch (not shown) is depressed by the user, the fan driving motor 421 is operated.

By the drive of the motor 421, the fan blades 420 are rotated, whereby air to be treated is taken into the fan casing 413 from the exterior through the air intake port 410a. The air to be treated is passed through the thin air layers b between the multi-stacked circular plates "a", "a" constituting the fan blades 420, in flowing from the inlet side toward the depth side through the central space SP formed internal to the circular plates "a", "a", and is discharged through an outlet port 440 to the exterior.

INDUSTRIAL APPLICABILITY (1) According to this invention, a self-blowing function is imparted to thin air layers by rotation of circular plates, in order to augment an air-blowing function and promote the treatment by an air-treating function of the plate surfaces. This construction makes it possible to cause separation of laminar flow, promoted turbulence of boundary layers near the plate surfaces due to an increased air velocity relative to the circular plate, propagating stall, etc. in the thin air layers. These phenomena, in turn, make it possible to activate remarkably the contact of air flow with one or more catalysts, deodorants, drying agents, fragrant agents, adsorbents or the like supported on, infiltrated in or otherwise possessed by a multiplicity of circular plates according to the respective uses intended. It is therefore possible to promote markedly the air-treating function according to the intended use.

(2) In addition, the rotation of circular plates constituting the plate fan causes air to make contact with the plate surface over an elongated distance and to flow along a logarithmic spiral path. This ensures that, even where the plate spacing is not uniform, a steady drift with respect to the circumferential direction is generated. Therefore, the total surface area of the circular plates can be used effectively, which also contributes to an increase in air-treating function.

(3) According to this invention, an air-treating block and an air-blowing fan block are united in one body, by providing the air-blowing fan block with an air-treating function. This enables the whole air treatment system to be made in a simple and compact construction, with an attendant large reduction in cost. Besides, the flow resistance which would be generated if a separate air-treating block were used is eliminated, so that the air treatment system can be constructed with a lower fan capacity, and with a large reduction in noise.

(4) Because the fan blades are composed of a multi-layered stack of circular plates and air is blown by centrifugal forces exerted thereon due to shearing forces acting between air and circular plates, the generation of turbulent-flow noise due to discharge of vortices on the downstream of the blades, usually experienced with sirocco fans and axial fans, is obviated and, hence, a silent fan operation can be achieved. Besides, even where the spacing of the stacked rotatable circular plates is reduced in order to increase the area per unit volume for contact of air with the functional agent, it is possible to promote markedly the air-treating function without any decrease in the flow rate of air through the air treatment system, because the self-blowing function by the rotation of the circular plates is increased. Consequently, it is possible to promote the contact between the functional agent (which is, for instance, supported on the circular plates) and the air being treated, and to further enhance the deodorizing capability while ensuring a silent operation and maintaining the compactness of the air treatment system.

(5) Moreover, deodorants having different constituents or different molecular structure can be supported on different circular plates (on a plate basis). Therefore, even where the odor generated in the interior of a toilet stool body is composed of a plurality of odorous components, a deodorizing effect can be ensured by selecting the most suitable deodorants for decomposition of the respective odorous components.

We claim:

1. Apparatus for performing air treatment functions, comprising:
   a plurality of circular plates stacked in a spaced-apart manner defining a stacked annular plate assembly having a central circular air inlet opening and a plurality of annular circular layers of air, each of said layers of air being between an adjacent pair of said annular plates and communicating with said central air inlet opening, spacings of said layer of air being determined to generate a laminar air flow upon rotation of said stacked annular plate assembly, said each annular circular solid plate having a flattened surface on both surfaces thereof;
   a plurality of vanes being interposed between said annular plates in a circumferentially spaced apart manner, said vanes extending radially and being operable as means for enhancing the propulsion of laminar air flow and for defining an accurate space between said annular plates;
   at least one composition of matter for effecting said air treatment function, exposed on a surface of at least one of said adjacent pairs of annular plates; and
   means for rotating said annular plates so that a spacing of said annular plates produces a centrifugal-blowing function utilizing centrifugal forces, resulting from circular movement of the air due to shear forces, and said air is expelled in a laminar flow from said stacked annular plate assembly along a logarithmic spiral path from said central air inlet opening to an outer circumferential periphery of said annular plates guided by said vanes;
   whereby said laminar flow of said air generates minimal noise and produces an amount of interaction between said at least one composition of matter and said air which is increased by a provision of said vanes.

2. Apparatus for treating air as in claim 1, wherein said at least one composition of matter is chosen from the group consisting essentially of catalysts, adsorbents, deodorants, fragrances, and drying agents.

3. Apparatus for treating air as in claim 1, wherein said at least one composition of matter is effective for decomposing foreign matter contained in said air.

4. Apparatus for treating air as in claim 1, wherein said at least one composition of matter is effective for removing foreign matter from said air.

5. Apparatus for treating air as in claim 1, wherein said at least one composition of matter is effective for deodorizing said air.

6. Apparatus for treating air as in claim 1, wherein said at least one composition of matter is effective for giving said air a fragrant odor.

7. Apparatus for treating air as in claim 1, wherein said at least one composition of matter is effective for drying said air.

8. Apparatus for treating air as in claim 1, wherein said each adjacent pair is separated by a distance $\delta$ whose value is determined from the following expression:

$$0.05 < \frac{\delta}{d_0 \cdot n \cdot (\tau \cdot D_{AB})^{\frac{1}{2}}} < 1.5 \ (s/m)$$

wherein
 $D_{AB}$ = diffusion coefficient of foreign matter (m²/s)
 $\tau$ = dwell time of air under treatment between said annular plates = (volume of air in said stacked annular plate assembly)/(flow rate of air through said stacked annular plate assembly)(s)
 $d_0$ = outside diameter of said stacked annular plates (m)
 n = rotational frequency (1/s or rps)
 $\delta$ = spacing between said adjacent pairs of annular plates (m).

9. Apparatus for treating air as in claim 1, wherein said at least one composition of matter is on at least one surface of at least one of said annular plates.

10. Apparatus for treating air as in claim 1, wherein at least one annular plate of said adjacent pairs of annular plates is comprised of said at least one composition of matter.

11. Apparatus for treating air as in claim 1, wherein said at least one composition of matter is a plurality thereof chosen from the group consisting essentially of catalysts, adsorbents, deodorants, fragrances, and drying agents.

12. Apparatus for treating air as in claim 1, wherein said at least one composition of matter is a combination of at least two thereof chosen from the group consisting essentially of catalysts, adsorbents, deodorants, fragrances, and drying agents.

13. Apparatus for treating air as in claim 1, wherein a heater is disposed along a path of said air entering said annular plates.

14. Apparatus for treating air as in claim 1, wherein said circular plates comprise metal.

15. Apparatus for treating air as in claim 1, wherein said circular plates comprise a nonwoven fabric.

16. Apparatus for treating air as in claim 1, wherein said circular plates comprise a fibrous material.

17. Apparatus for treating air as in claim 1, wherein said circular plates comprise a porous material.

18. Apparatus for treating air as in claim 1, wherein a plurality of vanes are interposed between said circular plates in a circumferentially spaced-apart manner.

19. Apparatus for treating air as in claim 18, wherein an outer end of each of said plurality of vanes is located at a predetermined distance radially inward from an outer circumferential edge of a one of said circular plates.

20. A method for treating air, comprising the steps of:
   stacking a plurality of annular plates, having smooth surfaces and at least one composition of matter effective for treating air embodied therein, in a spaced-apart manner to define a stacked plate assembly, including a plurality of vanes and a plurality of layers of air therebetween, each of said layers of air being between an adjacent pair of said annular plates; and
   rotating said annular plates to cause said air layers to manifest a centrifugal-blowing function generated by the effect of shearing forces upon said layers of air and resulting in a separation of laminar flow and a radial logarithmic spiral of air movement over said annular plates, whereby treatment of said air is promoted.

21. A method for treating air as in claim 23, wherein the step of embodying consists of affixing said at least one composition of matter to said at least one surface of at least one of said circular plates.

22. A method for treating air as in claim 23, wherein the step of embodying consists of forming said at least one circular plate of said at least one composition of matter.

23. A method for treating air as in claim 20, wherein said at least one composition of matter is chosen from the group consisting essentially of catalysts, adsorbents, deodorants, fragrances, and drying agents.

* * * * *